(12) United States Patent
Peel et al.

(10) Patent No.: US 10,738,084 B2
(45) Date of Patent: Aug. 11, 2020

(54) MACROCYCLES

(71) Applicant: Sentry Therapeutics Limited, Cambridge (GB)

(72) Inventors: Michael Peel, Chapel Hill, NC (US); Andrew Scribner, Durham, NC (US); Koichi Watashi, Tokyo (JP); Satomi Shimura, Zürich (CH)

(73) Assignee: Sentry Therapeutics Limited, Cambridge (GB)

( * ) Notice: Subject to any disclaimer, the term of this patent is extended or adjusted under 35 U.S.C. 154(b) by 67 days.

(21) Appl. No.: 15/740,747

(22) PCT Filed: Jun. 30, 2016

(86) PCT No.: PCT/US2016/040253
§ 371 (c)(1),
(2) Date: Dec. 28, 2017

(87) PCT Pub. No.: WO2017/004304
PCT Pub. Date: Jan. 5, 2017

(65) Prior Publication Data
US 2018/0186836 A1 Jul. 5, 2018

Related U.S. Application Data

(60) Provisional application No. 62/186,988, filed on Jun. 30, 2015.

(51) Int. Cl.
| C07K 7/64 | (2006.01) |
| A61P 31/20 | (2006.01) |
| A61K 38/13 | (2006.01) |
| A61K 38/00 | (2006.01) |

(52) U.S. Cl.
CPC .............. *C07K 7/645* (2013.01); *A61K 38/13* (2013.01); *A61P 31/20* (2018.01); *C07K 7/64* (2013.01); *A61K 38/00* (2013.01)

(58) Field of Classification Search
None
See application file for complete search history.

(56) References Cited

U.S. PATENT DOCUMENTS

2014/0212381 A1   7/2014 Li et al.

FOREIGN PATENT DOCUMENTS

WO    2013/181339 A2   12/2013

OTHER PUBLICATIONS

Farci et al. (Current and Future management of Chronic Hepatitis D Gastroenterol Hepatol (N.Y.) 2018, 14(6); 342-351).*
Dieden et al., "Cyclization reactions of IMM-125 and oxidation of cyclosporin A amino-acid 1 in the position of the double bond lead to the loss of in vitro immunosuppressive activity" Spectroscopy, vol. 14:215-228, 2000.
AC1LBFCW (Pubchem), Mar. 27, 2005, pp. 1-11; retrieved from internet https://pubchem.ncbi.nim.nih.gov/compound556984#section=inChiKey>; Aug. 31, 2016, p. 3.
International Search Report and Written Opinion, PCT/US2016/40253 dated Nov. 18, 2016.

* cited by examiner

*Primary Examiner* — James H Alstrum-Acevedo
*Assistant Examiner* — Tara L Martinez
(74) *Attorney, Agent, or Firm* — McCarter & English, LLP; Steven G. Davis; Mei Bai

(57) ABSTRACT

The invention relates to cyclic compounds of general formula (I): wherein $R^1$, $R^2$ and $R^3$ are as defined in the specification, and their use as pharmaceuticals.

(I)

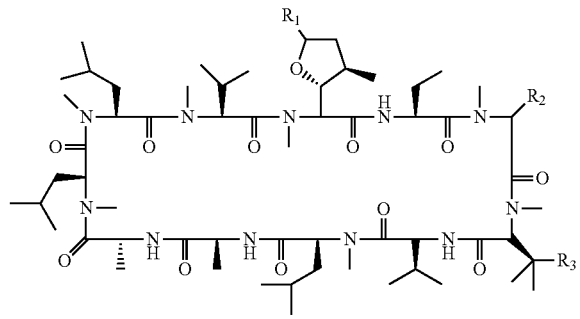

9 Claims, 5 Drawing Sheets

Specification includes a Sequence Listing.

MACROCYCLES

RELATED APPLICATION INFORMATION

This application is a 35 U.S.C. § 371 national stage filing of International Application No. PCT/US2016/040253, filed on Jun. 30, 2016, which claims the benefit of U.S. Provisional Application No. 62/186,988, filed on Jun. 30, 2015. The entire contents of each of the aforementioned applications are incorporated herein by reference in their entirety.

FIELD OF THE INVENTION

This invention relates to novel cyclosporine derivatives, compositions containing them, processes for their preparation, intermediates in their synthesis, and their use as therapeutics, for example as antiviral agents.

BACKGROUND OF THE INVENTION

Cyclosporine A is well known for its immunosuppressive activity and a range of therapeutic uses, including antifungal, anti-parasitic, and anti-inflammatory as well as anti-HIV activity. Cyclosporine A and certain derivatives have been reported to inhibit the replication of hepatitis B virus DNA and HBsAg production in-vitro, see Xie et al, *Acta Pharmacologica Sinica,* 2007, Vol. 28, pp 975-984; Gallay et al., *Gastroenterology* 2015, Vol. 148(2), pp 403-414. This activity has been proposed to be dependent on the ability of said cyclosporine derivatives to bind to, and to inhibit, cyclophilins, see Gallay et al.

Hepatitis B, and D, viruses infect hepatocytes via interaction with the membrane transporter, sodium taurocholate co-transporting polypeptide (NTCP), see Yan et al., *eLife* 2012, 00049. Cyclosporine A and certain derivatives have been reported to inhibit the interaction of HBV, and HDV, with NTCP to block infection of hepatocytes in-vitro, see Urban et al., *Journal of Hepatology* 2014, Vol. 60, pp 723-731; Watashi et al., *Hepatology* 2014, Vol. 59, pp 1726-1737. This activity of cyclosporine A, and certain derivatives, described as 'entry-inhibition', is reported to be independent of the well described ability of cyclosporine derivatives to inhibit cyclophilins see Watashi et al., *Hepatology* 2014, Vol. 59, pp 1726-1737.

Cyclosporine A (cyclosporine) derivatives modified in the 1-position (Bmt) to introduce a tetrahydrofuran ring are known in the literature. For example, 6-[(2S)—N-methyl-2-[tetrahydro-5-(2-hydroxyethyl)-3-methyl-2-furanyl]glycine]-cyclosporin A has been described as a metabolite produced in certain animals, and man, following administration of cyclosporine A, see Maurer et al., *Drug Metab. Dispos.,* 1984, 12, 120. The biological activity of this compound is described by Freed et al., *Transplantation Proceed.* 1991, vol. 23, pp 980-981. 6-[(2S)—N-methyl-2-[tetrahydro-5-(1-hydroxyethyl)-3-methyl-2-furanyl]glycine]-cyclosporin A is described by Liu et al., *Clinical Biochemistry* 1998, 31, 173-180 and was evaluated for immunosuppressive activity by Durette et al., *Transplantation Proceed.* 1988, vol. 2, pp 51-57. 6-[(2S)—N-methyl-2-[tetrahydro-5-(1-iodoethyl)-3-methyl-2-furanyl]glycine]-cyclosporin A is described as a reagent for cyclophilin binding assays and structural studies by Petcher et al., *Helv. Chim. Acta.* 1976, 59, 1480-8 and Mahony et al., *Clinical Chemistry* (Washington, D.C., USA) 1985, 31, 459-462. 6-[(2S)—N-methyl-2-[tetrahydro-5-(1-hydroxy-2-propenyl)-3-methyl-2-furanyl]glycine]-cyclosporin A is produced by microbial transformation as described by Freitag et al. in WO 2006066416. No antiviral activity is described for these compounds.

SUMMARY OF THE INVENTION

In one aspect the invention provides a cyclosporine derivative of general formula (I):

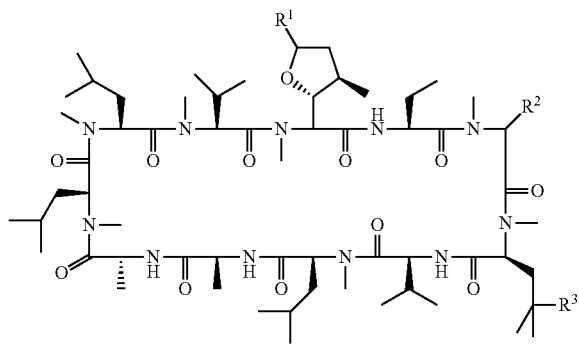

(I)

wherein:

$R^1$ represents hydrogen; alkyl, preferably $C_1$-$C_6$-alkyl, optionally substituted with 1 to 3 substituents independently selected from $OR^4$ or halogen; and alkenyl, preferably $C_2$-$C_6$-alkenyl, optionally substituted with 1 to 3 substituents independently selected from $OR^4$ or halogen;

$R^2$ represents hydrogen; alkyl, preferably $C_1$-$C_6$-alkyl; and $XR^5$;

$R^3$ represents hydrogen or hydroxyl, with the proviso that when $R^2$ and $R^3$ are both hydrogen then $R^1$ cannot be —$CH_2CH_2OH$, —$CH(OH)CH_3$, —$CH(I)CH_3$ or —$CH(OH)CH=CH_2$;

X represents sulfur or oxygen;

$R^4$ represents alkyl, preferably $C_1$-$C_3$-alkyl;

$R^5$ represents straight- or branched-chain alkyl, preferably having from one to six carbon atoms, optionally substituted by one or more groups selected from the group consisting of halogen; hydroxy; alkoxy; and —$NR^6R^7$;

$R^6$ and $R^7$, which may be the same or different, each represent:
  hydrogen; methyl; and ethyl;
  or $R^4$ and $R^5$, together with the nitrogen atom to which they are attached, form a saturated or unsaturated heterocyclic ring containing from four to six ring atoms, which ring may optionally contain another heteroatom selected from the group consisting of nitrogen, oxygen and sulfur;
  or a pharmaceutically acceptable salt or solvate thereof.

In certain cases the substituents $R^1$ and $R^2$ may contribute to optical and/or stereoisomerism. All such forms are embraced by the present invention.

In another aspect, provided are compositions comprising a compound provided herein along with a pharmaceutically acceptable excipient, carrier or diluent.

In another aspect, provided are pharmaceutically acceptable salts of a compound provided herein. Examples of pharmaceutically acceptable salts include salts with alkali metals, e.g., sodium, potassium or lithium, or with alkaline-earth metals, e.g., magnesium or calcium, the ammonium salt or the salts of nitrogenous bases, e.g., ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine or dibenzylamine.

In another aspect, provided are methods of using a compound or composition provided herein to treat or prevent an infection caused by the hepatitis B or hepatitis D virus. The methods generally comprise administering to a subject having the condition or disease an amount of the compound or composition effective to treat or prevent the disease or condition.

DETAILED DESCRIPTION

DEFINITIONS

Figure 1:
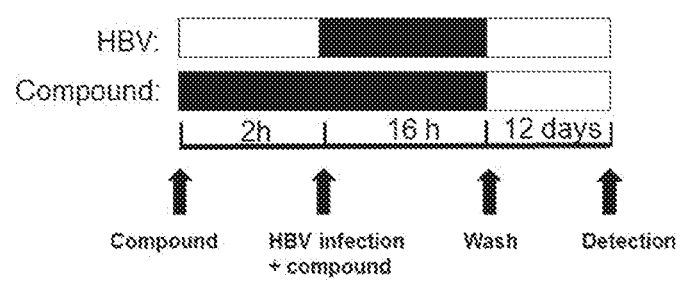
FIG. 1 shows a representative procedure for testing compounds of the invention for activity as HBV entry inhibitors.

When referring to the compounds and complexes of the invention, the following terms have the following meanings unless indicated otherwise.

"Cyclosporine" refers to any cyclosporine compound known to those of skill in the art, or a derivative thereof. See, e.g., Ruegger et al., 1976, *Helv. Chim. Acta.* 59:1075-92; Borel et al., 1977, *Immunology* 32:1017-25; the contents of which are hereby incorporated by reference in their entireties. Exemplary compounds of the invention are cyclosporine derivatives. Unless noted otherwise, a cyclosporine described herein is a cyclosporine A, and a cyclosporine derivative described herein is a derivative of cyclosporine A.

The cyclosporine nomenclature and numbering systems used hereafter are those used by J. Kallen et al., "Cyclosporins: Recent Developments in Biosynthesis, Pharmacology and Biology, and Clinical Applications", Biotechnology, second edition, H.-J. Rehm and G. Reed, ed., 1997, p 535-591 and are shown below:

| Position | Amino acid in cyclosporine A |
|---|---|
| 1 | N-Methyl-butenyl-threonine (MeBmt) |
| 2 | [alpha]-aminobutyric acid (Abu) |
| 3 | Sarcosine (Sar) |
| 4 | N-Methyl-leucine (MeLeu) |

| Position | Amino acid in cyclosporine A |
|---|---|
| 5 | Valine (Val) |
| 6 | N-Methyl-leucine (MeLeu) |
| 7 | Alanine (Ala) |
| 8 | (D)-Alanine ((D)-Ala) |
| 9 | N-Methyl-leucine (Me-Leu) |
| 10 | N-Methyl-leucine (MeLeu) |
| 11 | N-Methylvaline (MeVal) |

This corresponds to the saturated ring carbon atoms in the compounds of formula (I) as shown below:

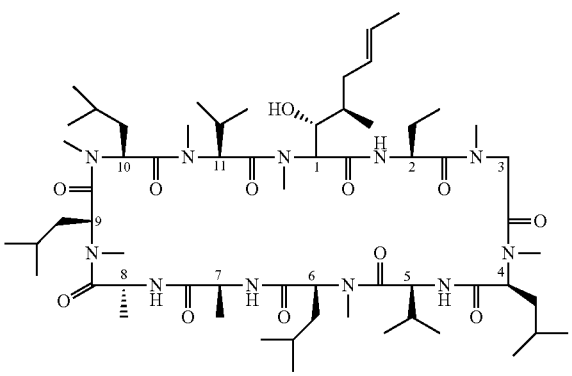

"Alkyl" refers to monovalent saturated aliphatic hydrocarbyl groups particularly having up to 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like.

"Alkenyl" refers to monovalent olefinically unsaturated hydrocarbyl groups, in one embodiment, having up to 11 carbon atoms, in other embodiment, from 2 to 8 carbon atoms, and in another embodiment, from 2 to 6 carbon atoms, which can be straight-chained or branched and having at least 1 or from 1 to 2 sites of olefinic unsaturation. In some embodiments, alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Cycloheteroalkyl" refers to a ring containing from 4 to 6 ring atoms and from 1 to 4 heteroatoms which may be the same or different selected from nitrogen, oxygen and sulphur.

A "saturated or unsaturated ring containing from 4 to 6 ring atoms" refers to a ring containing only carbon atoms, or a heterocyclic ring containing carbon atoms and non-carbon atoms (e.g. N).

"Optionally substituted" when describing a substituent refers to a substitution of a hydrogen atom which would otherwise be present on the substituent. When discussing ring systems, the optional substitution is typically with 1, 2 or 3 substituents replacing the normally-present H. However, when discussing straight (including branched) moieties, the number of substitutions can be more, occurring wherever a H is usually present. The substitutions can be the same or different. Typical substitutions can be e.g. nitro, —NR'R"', cyano, —NR'COR"', alkyl, —SO$_2$R"', —NR'SO$_2$R"', —SO$_2$NRR"', —CONR'R"', —CONHC$_6$H$_5$, hydroxy, alkoxy, haloalkyl, haloalkoxy, mercapto (—SH), thioalkyl and halogen, where R' and R", which are the same or different, each represent hydrogen or alkyl; or when R' and R" are each attached to a nitrogen atom, they may form a saturated or unsaturated heterocyclic ring containing from 4 to 6 ring atoms, and wherein R is alkyl or haloalkyl.

"Alkoxy" refers to the group —OR where R is alkyl. The alkyl group has up to 11 carbon atoms, more particularly as a lower alkyl, from 1 to 8 carbon atoms and still more particularly, from 1 to 6 carbon atoms. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"N-Alkylamino" refers to the group H—NR'—, wherein R' is selected from hydrogen and alkyl. The alkyl group has up to 11 carbon atoms, more particularly as a lower alkyl, from 1 to 8 carbon atoms and still more particularly, from 1 to 6 carbon atoms.

"Alkoxycarbonyl" refers to a radical —C(=O)-alkoxy where alkoxy is as defined herein.

"Allyl" refers to the radical $H_2C=C(H)-C(H_2)-$.

"Amino" refers to the radical $-NH_2$.

"Bmt" refers to 2(S)-amino-3(R)-hydroxy-4(R)-methyl-6 (E)-octenoic acid.

"Cpd" means compound.

"Carboxyl" refers to the radical —C(=O)OH.

"N,N-Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Halogen" or "halo" refers to chloro, bromo, fluoro or iodo.

"Hydroxy" refers to the radical —OH.

"Thioalkyl" refers to the group —SR where R is alkyl. The alkyl group has up to 11 carbon atoms, more particularly as a lower alkyl, from 1 to 8 carbon atoms and still more particularly, from 1 to 6 carbon atoms. Examples include, but are not limited to, methylthio, ethylthio, propylthio, butylthio, and the like.

"Pharmaceutically acceptable salt" refers to any salt of a compound of this invention which retains its biological properties and which is not toxic or otherwise undesirable for pharmaceutical use. Such salts may be derived from a variety of organic and inorganic counter-ions well known in the art. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations and the like.

"Solvate" refers to a compound of the present invention or a salt thereof that further includes a stoichiometric or non-stoichiometric amount of solvent bound by non-covalent intermolecular forces. Where the solvent is water, the solvate is a hydrate.

It is to be understood that compounds having the same molecular formula but differing in the nature or sequence of bonding of their atoms or in the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78:413-447, *Angew. Chem., Int. Ed. Engl.* 5:385-414 (errata: *Angew. Chem., Int. Ed. Engl.* 5:511); Prelog and Helmchen, 1982, *Angew. Chem.* 94:614-631, *Angew. Chem. Internat. Ed. Eng.* 21:567-583; Mata and Lobo, 1993, *Tetrahedron: Asymmetry* 4:657-668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture".

In certain embodiments, the compounds of this invention may possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, the present invention provides the stereoisomers of the compounds depicted herein upon treatment with base.

In certain embodiments, the compounds of the invention are "stereochemically pure". A stereochemically pure compound has a level of stereochemical purity that would be recognized as "pure" by those of skill in the art. Of course, this level of purity will be less than 100%. In certain embodiments, "stereochemically pure" designates a compound that is substantially free of alternate isomers. In particular embodiments, the compound is 85%, 90%, 91%, 92%, 93%, 94%, 95%, 96%, 97%, 98%, 99%, 99.5% or 99.9% free of other isomers.

"Sarcosine" or "Sar" refers to the amino acid residue known to those of skill in the art having the structure —N(Me)CH$_2$C(=O)—. Those of skill in the art might recognize sarcosine as N-methyl glycine.

As used herein, the terms "subject" and "patient" are used interchangeably herein. The terms "subject" and "subjects" refer to an animal, in some embodiments, a mammal including a non-primate (e.g., a cow, pig, horse, cat, dog, rat, and mouse) and a primate (e.g., a monkey such as a cynomolgous monkey, a chimpanzee and a human), and a human. In another embodiment, the subject is a farm animal (e.g., a horse, a cow, a pig, etc.) or a pet (e.g., a dog or a cat). In one embodiment, the subject is a human.

As used herein, the terms "therapeutic agent" and "therapeutic agents" refer to any agent(s) which can be used in the treatment, management, or amelioration of a disorder or one or more symptoms thereof. In certain embodiments, the term "therapeutic agent" refers to a compound of the invention. In certain other embodiments, the term "therapeutic agent" does not refer to a compound of the invention. In one embodiment, a therapeutic agent is an agent that is known to be useful for, or has been or is currently being used for the treatment, management, prevention, or amelioration of a disorder or one or more symptoms thereof.

"Therapeutically effective amount" means an amount of a compound or complex or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"THF" means tetrahydrofuran.

"Treating" or "treatment" of any disease or disorder refers, in one embodiment, to ameliorating a disease or disorder that exists in a subject. In another embodiment, "treating" or "treatment" refers to ameliorating at least one physical parameter, which may be indiscernible by the subject. In yet another embodiment, "treating" or "treatment" refers to modulating the disease or disorder, either physically (e.g., stabilization of a discernible symptom) or physiologically (e.g., stabilization of a physical parameter) or both. In yet another embodiment, "treating" or "treatment" refers to delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" refers to a compound of the invention. In certain other embodiments, the term "prophylactic agent" does not refer a compound of the invention. In one embodiment, a prophylactic agent is an agent which is known to be useful for, or has been or is currently being used to prevent or impede the onset, development, progression and/or severity of a disorder.

As used herein, the terms "prevent", "preventing" and "prevention" refer to the prevention of the recurrence, onset, or development of one or more symptoms of a disorder in a subject resulting from the administration of a therapy (e.g., a prophylactic or therapeutic agent), or the administration of a combination of therapies (e.g., a combination of prophylactic or therapeutic agents).

As used herein, the phrase "prophylactically effective amount" refers to the amount of a therapy (e.g., prophylactic agent) which is sufficient to result in the prevention of the development, recurrence or onset of one or more symptoms associated with a disorder, or to enhance or improve the prophylactic effect(s) of another therapy (e.g., another prophylactic agent).

The term "label" refers to a display of written, printed or graphic matter upon the immediate container of an article, for example the written material displayed on a vial containing a pharmaceutically active agent.

The term "labeling" refers to all labels and other written, printed or graphic matter upon any article or any of its containers or wrappers or accompanying such article, for example, a package insert or instructional videotapes or DVDs accompanying or associated with a container of a pharmaceutically active agent.

Compounds

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

In one embodiment, $R^1$ represents hydrogen; $C_1$-$C_6$-alkyl optionally substituted with 1 to 3 substituents independently selected from $OR^4$ or halogen; and $C_2$-$C_6$-alkenyl optionally substituted with 1 to 3 substituents independently selected from $OR^4$ or halogen. In a further embodiment, $R^1$ represents $C_1$-$C_3$ alkyl optionally substituted with hydroxyl. In further embodiments $R^1$ represents —CH$_2$CH$_3$ and —CH$_2$CH$_2$OH. In further embodiments, R$^1$ represents C$_1$-C$_3$ alkenyl. In further embodiments R$^1$ represents —CH=CH$_2$ In certain embodiment, R$^2$ represents hydrogen; C$_1$-C$_6$-alkyl; and XR$^5$. In certain embodiments, R$^2$ represents C$_1$-C$_3$-alkyl. In certain embodiments, R$^2$ represents methyl. In certain embodiments, R$^2$ represents X—(C$_1$-C$_6$-alkyl) NR$^6$R$^7$, wherein X represents sulfur. In further embodiments R$^2$ represents S—(CH$_2$CH$_2$) NR$^6$R$^7$, wherein R$^6$R$^7$ may be the same or different, each represent hydrogen or straight- or branched-chain alkyl having from one to three carbon atoms. In further embodiments R$^2$ represents S—(CH$_2$CH$_2$) NMe$_2$ R$^3$ represents hydrogen or hydroxyl, with the exception that when R$^2$ and R$^3$ are both hydrogen then R$^1$ cannot be —CH$_2$CH$_2$OH, —CH(OH)CH$_3$, —CH(I)CH$_3$ or —CH(OH)CH=CH$_2$. In further embodiments, R$^3$ is hydroxyl.

In one embodiment, the compound provided herein is selected from the following compounds of Table 1:

TABLE 1

| Example A | 1-[(2S)-N-Methyl-2-[tetrahydro-5-ethyl-3-methyl-2-furanyl]glycine]-cyclosporin A |
| Example B | 1-[(2S)-N-methyl-2-[tetrahydro-5-ethenyl-3-methyl-2-furanyl]glycine]-cyclosporin A |
| Example C | 1-[(2S)-N-methyl-2-[tetrahydro-5-ethyl-3-methyl-2-furanyl]glycine]4-(4-hydroxy-N-methyl-L-leucine)-cyclosporin A |
| Example D | 1-[(2S)-N-methyl-2-[tetrahydro-5-ethenyl-3-methyl-2-furanyl]glycine]--4-(4-hydroxy-N-methyl-L-leucine)-cyclosporin A |
| Example E | 1-[(2S)-N-methyl-2-[tetrahydro-5-(2-hydroxyethyl)-3-methyl-2-furanyl]glycine]-4-(4-hydroxy-N-methyl-L-leucine)-cyclosporin A |
| Example F | 1-[(2S)-N-methyl-2-[tetrahydro-5-ethyl-3-methyl-2-furanyl]glycine]-3-[2R-[[2-(dimethylamino)eth-yl]thio]-N-methylglycine]-4-(4-hydroxy-N-methyl-L-leucine)-cyclosporin A |
| Example G | 1-[(2S)-N-methyl-2-[tetrahydro-5-ethenyl-3-methyl-2-furanyl]glycine]-3-[2R-[[2-(dimethylamino)eth-yl]thio]-N-methylglycine]-4-(4-hydroxy-N-methyl-L-leucine)-cyclosporin A |
| Example H | 1-[(2S)-N-methyl-2-[tetrahydro-5-(2-hydroxyethyl)-3-methyl-2-furanyl]glycine]-3-[2R-[[2-(dimethyl-amino)ethyl]thio]-N-methylglycine]-4-(4-hydroxy-N-methyl-L-leucine)-cyclosporin A |

The letters A to H are used to identify the above compounds hereafter.

The compounds of the invention can be prepared, isolated or obtained by any method apparent to those of skill in the art. Exemplary methods of preparation are described in detail in the examples below.

According to a feature of the present invention compounds of formula (I) may be prepared from compounds of general formula II by selective modification of the group X. Preferably the group X is an arylselenium (ArSe), arylthio (ArS), halogen, hydroxy or mercury. More preferably the group X is phenylselenyl (PhSe) or phenylthio (PhS).

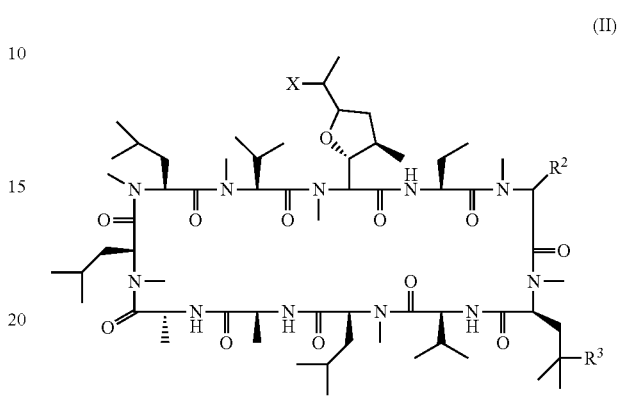

Treatment with compounds of general formula II with a reducing agent transforms the X group into a hydrogen and leads to compounds of formula I in which R$^1$ is ethyl. Preferred reducing agents include, but are not limited to, sodium/ammonia, mercury amalgam, tributyltin hydride and the like.

Alternatively, treatment of compounds of general formula II, wherein X is phenylselenyl or phenythio, with a selective oxidation agent in an appropriate solvent, followed by heating the solution results in elimination of the X group with concomitant introduction of a carbon-carbon double bond and leads to compounds of formula I in which R$^1$ is ethenyl. Preferred oxidation agents include sodium periodate, m-chloroperoxybenzoic acid and the like and the intermediate selenoxide/sulfoxide is preferably heated to between 25-80° C. Further transformation of compounds of formula I in which R$^1$ is ethenyl can be achieved by, for example, subjecting said compounds to conditions known to effect a hydroboration reaction. Oxidation of the product of hydroboration leads to compounds of formula I in which R$^1$ is —(CH$_2$CH$_2$)OH. Preferred hydroboration reagents include borane-THF, dicyclohexylborane and 9-BBN.

Alternatively, treatment of compounds of general formula II, wherein X is hydroxyl with a base followed by an alkylating agent, such as methyl iodide leads to compounds of general formula I in which R$^1$ is CH(OR$^4$)CH$_3$ and R$^4$ is methyl. Further, oxidation of compounds of general formula II, wherein X is hydroxyl, with reagents known to convert a hydroxyl to a carbonyl group, affords a ketone that can be elaborated using well established methods to compounds of formula I in which R1 is a substituted or unsubstituted alkylene and a substituted or unsubstituted alkyl. Preferred reagents for effecting such transformations include, but are not limited to phosphonium ylid salts, phosphonate reagents, anionic silicon reagents and the like.

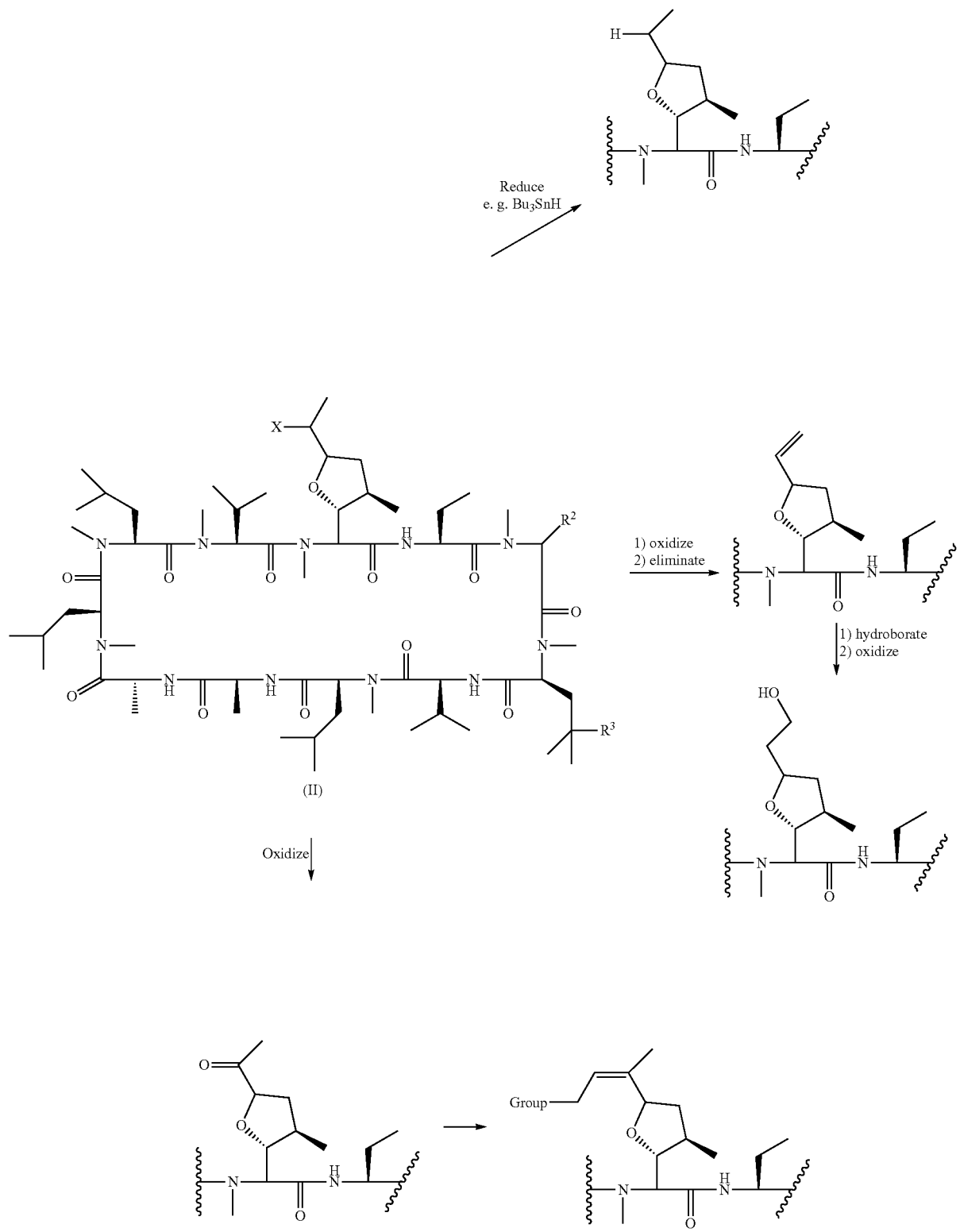

According to a feature of the present invention compounds of formula (II) may be prepared by causing a cyclization of a compound of formula (III):

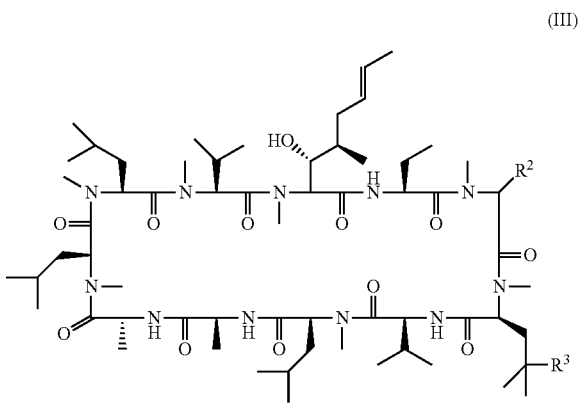

(III)

Said cyclization may be conveniently be achieved by treatment of compounds of formula III with an electrophilic reagent in an appropriate solvent. The electrophilic agent is selected such that an X group is introduced into the cyclized product of formula II. Preferably the electrophilic agent is phenylselenenyl chloride or bromide (X=PhSe), phenylsulfenyl chloride or bromide (X=PhS), N-bromosuccinimide (X=Br), iodine (X=I), hydrogen peroxide (X=OH) and mercury II acetate (X=HgOAc).

Compounds of general formula III in which $R^2$ is C1-C6-alkyl; and $XR^5$ can be conveniently from cyclosporin A and 4-(4-hydroxy-N-methyl-L-leucine)-cyclosporin A by a sequence involving treatment of cyclosporin A or 4-(4-hydroxy-N-methyl-L-leucine)-cyclosporin A with a strong base in an inert solvent to generate an appropriate enolate and reacting said enolate with an electrophile. Use of a C1-C6 alkyl halide as the electrophile results in compounds of formula III in which $R^2$ is a C1-C6 alkyl group. Using a substituted disulphide reagent, such as N,N,N',N' tetramethylcystamine, as the electrophile results in the preparation of compounds of general formula III in which $R^2$ is $XR^5$ wherein X is sulfur and $R^5$ is —$(CH_2CH_2)NMe_2$. Conversion of cyclosporine A and 4-(4-hydroxy-N-methyl-L-leucine)-cyclosporin A into compounds of general formula III has been described in Barriere et al., *Bioorganic & Medicinal Chemistry Letters*, 2003, Vol. 13, pp. 4415-4419; Seebach et al., *Helvetica Chimica Acta* 1993, Vol. 76, pp. 1564-1590.

Where a compound of the present invention, e.g. a compound of the invention, is substituted with a basic moiety, an acid addition salt can be formed. The acid which can be used to prepare an acid addition salt includes that which produces, when combined with the free base, a pharmaceutically acceptable salt, that is, a salt whose anion is non-toxic to a subject in the pharmaceutical doses of the salt. Pharmaceutically acceptable salts within the scope of the invention are those derived from the following acids: mineral acids such as hydrochloric acid, hydrobromic acid, sulfuric acid, phosphoric acid, sulfamic acid and nitric acid; and organic acids such as acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids.

According to a further feature of the invention, acid addition salts of the compounds of this invention can be prepared by reaction of the free base with the appropriate acid, by the application or adaptation of known methods. For example, the acid addition salts of the compounds of this invention can be prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Where a compound of the invention is substituted with an acid moiety, base addition salts can be formed. Pharmaceutically acceptable salts, including for example alkali and alkaline earth metal salts, within the scope of the invention are those derived from the following bases: sodium hydride, sodium hydroxide, potassium hydroxide, calcium hydroxide, magnesium hydroxide, aluminum hydroxide, lithium hydroxide, zinc hydroxide, barium hydroxide, and organic amines such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutical Compositions and Methods of Administration

The cyclosporine compounds used in the method of the present invention can be administered in certain embodiments using pharmaceutical compositions containing at least one compound of general formula (I), if appropriate in the salt form, either used alone or in the form of a combination with one or more compatible and pharmaceutically acceptable carriers, such as diluents or adjuvants. In clinical practice the cyclosporine compounds of the present invention may be administered by any conventional route, in particular orally, parenterally, rectally or by inhalation (e.g. in the form of aerosols). In one embodiment, the cyclosporine compounds of the present invention are administered orally.

As well as compounds described herein being useful in pharmaceutical compositions and in methods of treatment of diseases and as antiviral agents, in further embodiments of the invention, there is provided a cyclosporine derivative of general formula (I):

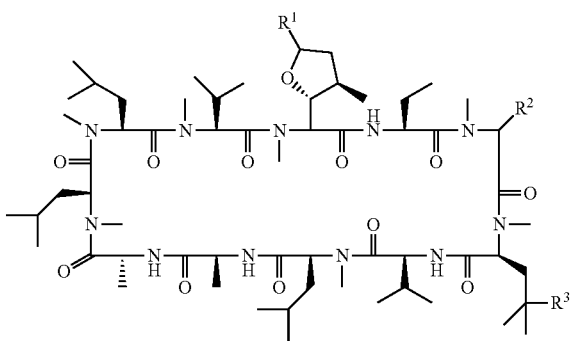

(I)

wherein:
- R¹ represents hydrogen; alkyl, preferably $C_1$-$C_6$-alkyl, optionally substituted with 1 to 3 substituents independently selected from OR⁴ or halogen; and alkenyl, preferably $C_2$-$C_6$-alkenyl, optionally substituted with 1 to 3 substituents independently selected from OR⁴ or halogen;
- R² represents hydrogen; alkyl, preferably $C_1$-$C_6$-alkyl; and XR⁵;
- R³ represents hydrogen or hydroxyl;
- X represents sulfur or oxygen;
- R⁴ represents alkyl, preferably $C_1$-$C_3$-alkyl;
- R⁵ represents straight- or branched-chain alkyl, preferably having from one to six carbon atoms, optionally substituted by one or more groups selected from the group consisting of halogen; hydroxy; alkoxy; and —NR⁶R⁷;
- R⁶ and R⁷, which may be the same or different, each represent:
  - hydrogen; methyl; and ethyl;
  - or R⁴ and R⁵, together with the nitrogen atom to which they are attached, form a saturated or unsaturated heterocyclic ring containing from four to six ring atoms, which ring may optionally contain another heteroatom selected from the group consisting of nitrogen, oxygen and sulfur;

or a pharmaceutically acceptable salt or solvate thereof, for use in a pharmaceutical composition and/or for use as an antiviral agent and/or for the treatment of disease (such as HBV and HDV).

Use may be made, as solid compositions for oral administration, of tablets, pills, hard gelatin capsules, powders or granules. In these compositions, the active product according to the invention is mixed with one or more inert diluents or adjuvants, such as sucrose, lactose or starch.

These compositions can comprise substances other than diluents, for example a lubricant, such as magnesium stearate, or a coating intended for controlled release Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In one embodiment, a composition of the invention is a pharmaceutical composition or a single unit dosage form. Pharmaceutical compositions and single unit dosage forms of the invention comprise a prophylactically or therapeutically effective amount of one or more prophylactic or therapeutic agents (e.g., a compound of the invention, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In certain embodiments, water is a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E.W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions of the invention can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are, in certain embodiments, anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in one embodiment, in purified form, together with a suitable amount of carrier so as to provide the form for proper administration to the subject. The formulation should suit the mode of administration. In one embodiment, the pharmaceutical compositions or single unit dosage forms are sterile and in suitable form for administration to a subject, such as an animal subject, in one embodiment, a mammalian subject, such as a human subject.

A pharmaceutical composition of the invention is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms of the invention will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 20th ed., Mack Publishing, Easton Pa. (2000).

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms of the invention comprise a compound of the invention, or a pharmaceutically acceptable salt, solvate or hydrate thereof lie within the range of from about 0.1 mg to about 1000 mg per day, given as a single once-a-day dose in the morning or in one aspect, as divided doses throughout the day taken with food. In certain embodiments, dosage forms of the invention have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active cyclosporine.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

See generally, *Remington's Pharmaceutical Sciences,* 20th ed., Mack Publishing, Easton Pa. (2000).

In certain embodiments, the oral dosage forms are solid and prepared under anhydrous conditions with anhydrous ingredients, as described in detail in the sections above. However, the scope of the invention extends beyond anhydrous, solid oral dosage forms. As such, further forms are described herein.

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC 581. Suitable anhydrous or low moisture excipients or additives include AVICEL PH 103 and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In one embodiment, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

Although solid, anhydrous oral dosage forms can be used, the present invention also provides parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are, in one embodiment, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical & Mucosal Dosage Forms

In one embodiment, solid, anhydrous oral dosage forms can be used. In another aspect, provided herein are transdermal, topical, and mucosal dosage forms. Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980, 1990 & 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980, 1990 & 2000).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Methods of Treating or Preventing Disease in a Subject

The compounds of the present invention act to inhibit the entry of hepatitis B and hepatitis D into cells by interfering with the sodium taurocholate co-transporting peptide receptor. The anti-HBV and HDV effect is independent of binding to cyclophilins or calcineurin such that the compounds of the invention would be expected to have none of the immunosuppressive activity associated with cyclosporine A itself. Some compounds of the invention show anti-HBV entry activity against multiple different HBV genotypes, including A, B and C. Further, compounds of the invention show anti-HBV entry activity against nucleoside resistant forms of HBV, in particular against Entecavir® resistant HBV.

Dosage and Unit Dosage Forms

In human therapeutics, the doctor will determine the posology which he considers most appropriate according to a preventive or curative treatment and according to the age, weight, stage of the infection and other factors specific to the subject to be treated. Generally, doses are from about 1 to about 1500 mg per day for an adult, or from about 50 to about 1300 mg per day or from about 100 to 1100 mg per day for an adult In one embodiment, dose rates are from about 250 to about 1000 mg per day.

In further aspects, the present invention provides methods of treating or preventing HBV or HBV/HDV infection in a subject by administering, to a subject in need thereof, an effective amount of a compound of the invention, or a pharmaceutically acceptable salt thereof.

The amount of the compound or composition of the invention which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

Exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions of the invention, the dosage administered to a subject is typically 0.140 mg/kg to 3 mg/kg of the subject's body weight, based on weight of the active compound. In certain aspects, the dosage administered to a subject is between 0.20 mg/kg and 2.00 mg/kg, or between 0.30 mg/kg and 1.50 mg/kg of the subject's body weight.

In general, the recommended daily dose range of a composition of the invention for the conditions described herein lie within the range of from about 0.1 mg to about 1500 mg per day, given as a single once-a-day dose or as divided doses throughout a day. In one embodiment, the daily dose is administered twice daily in equally divided doses. Specifically, a daily dose range should be from about 50 mg to about 1300 mg per day, more specifically, between about 100 mg and about 1100 mg per day, or even more specifically between about 250 and about 1000 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition of the invention are also encompassed by the above described dosage amounts and dose frequency schedules. Further, when a subject is administered multiple dosages of a composition of the invention, not all of the dosages need be the same. For example, the dosage administered to the subject may be increased to improve the prophylactic or therapeutic effect of the composition or it may be decreased to reduce one or more side effects that a particular subject is experiencing.

In a specific embodiment, the dosage of the composition of the invention or a composition of the invention, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition of the invention or a composition of the invention administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition of the invention followed by one or more maintenance doses. In such embodiments, the loading dose can be, for instance, about 60 to about 400 mg per day, or about 100 to about 200 mg per day for one day to, forty-eight weeks, or from one day to five weeks. The loading dose can be followed by one or more maintenance doses. Each maintenance does can be, independently, about from about 5 mg to about 1500 mg per day, or from about 10 mg to about 200 mg per day, more specifically, between about 25 mg and about 150 mg per day, or even more specifically between about 25 and about 80 mg per day. In certain embodiment, maintenance doses are administered daily and can be administered as single doses, or as divided doses.

In certain embodiments, a dose of a compound or composition of the invention can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition of the invention is administered to achieve a steady-state concentration in blood or serum of the subject of from about 300 to about 4000 ng/mL, from about 400 to about 1600 ng/mL, or from about 600 to about 1200 ng/mL. Loading doses can be administered to achieve steady-state blood or serum concentrations of about 1200 to about 8000 ng/mL, or about 2000 to about 4000 ng/mL for one to five days. Maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, the present invention provides unit dosages comprising a compound of the invention, or a pharmaceutically acceptable salt thereof, in a form suitable for administration. Such forms are described in detail above. In certain embodiments, the unit dosage comprises 1 to 1500 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

Combination Therapy

The present invention provides methods of treatment or prevention that comprise the administration of a second agent effective for the treatment or prevention of HBV or HBV/HDV infection in a subject in need thereof. The second agent can be any agent known to those of skill in the art to be effective for the treatment or prevention of the HBV or HBV/HDV infection. The second agent can be a second agent presently known to those of skill in the art, or the second agent can be second agent later developed for the treatment or prevention of HBV or HBV/HDV.

In certain embodiments, a compound of the invention is administered in combination with one second agent. In further embodiments, a second agent is administered in combination with two second agents. In still further embodiments, a second agent is administered in combination with two or more second agents.

Suitable second agents include injectable protein therapeutics or small-molecule, orally bioavailable inhibitors of HBV. Exemplary second agents include Intron A (interferon α-2b), Pegasys (peginterferon α-2a), Epivir-HBV (Lamivudine), Hepsera (Adefovir Dipivoxil), Baraclude (Entecavir), Tyzeka (Telbivudine), Viread (Tenofovir).

In certain embodiments, the second agent of the invention can be formulated or packaged with the cyclosporine derivatives of the invention. Of course, the second agent will only be formulated with the cyclosporine derivative of the present invention when, according to the judgment of those of skill in the art, such co-formulation should not interfere with the activity of either agent or the method of administration. In certain embodiment, the cyclosporine derivative of the invention and the second agent are formulated separately. They can be packaged together, or packaged separately, for the convenience of the practitioner of skill in the art.

The dosages of the second agents are to be used in the combination therapies of the invention. In certain embodiments, dosages lower than those which have been or are currently being used to prevent or treat HBV or HBV/HDV infection are used in the combination therapies of the invention. The recommended dosages of second agents can obtained from the knowledge of those of skill. For those second agents that are approved for clinical use, recommended dosages are described in, for example, Hardman et al., eds., 1996, Goodman & Gilman's The Pharmacological Basis Of Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J., which are incorporated herein by reference in its entirety.

In various embodiments, the therapies (e.g., the cyclosporine derivative of the invention and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In certain embodiments, two or more therapies are administered within the same patent visit.

In certain embodiments, the cyclosporine derivative of the invention and the second agent are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a cyclosporine derivative of the invention and a second agent are administered to a patient, for example, a mammal such as a human, in a sequence and within a time interval such that the cyclosporine derivative can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the cyclosporine derivative and the second active agent exert their effect at times which overlap. Each second active agent can be administered separately, in any appropriate form and by any suitable route. In other embodiments, the cyclosporine derivative is administered before, concurrently or after administration of the second active agent.

In various embodiments, the cyclosporine derivative and the second agent are administered less than about 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In other embodiments, the cyclosporine derivative and the second agent are administered concurrently.

In other embodiments, the cyclosporine derivative and the second agent are administered at about 2 to 4 days apart, at about 4 to 6 days apart, at about 1 week part, at about 1 to 2 weeks apart, or more than 2 weeks apart.

In certain embodiments, the cyclosporine derivative and the second agent are cyclically administered to a patient. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improve the efficacy of the treatment.

In certain embodiments, the cyclosporine derivative and the second active agent are administered in a cycle of less than about 3 weeks, about once every two weeks, about once every 10 days or about once every week. One cycle can comprise the administration of a cyclosporine derivative and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the cyclosporine derivative can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the cyclosporine derivative. In one embodiment, a cyclosporine derivative is administered concurrently with one or more second agents in the same pharmaceutical composition. In another embodiment, a cyclosporine derivative is administered concurrently with one or more second agents in separate pharmaceutical compositions. In still another embodiment, a cyclosporine derivative is administered prior to or subsequent to administration of a second agent. The invention contemplates administration of a cyclosporine derivative and a second agent by the same or different routes of administration, e.g., oral and parenteral. In certain embodiments, when a cyclosporine derivative is administered concurrently with a second agent that potentially produces adverse side effects including, but not limited to, toxicity, the second active agent can advantageously be administered at a dose that falls below the threshold that the adverse side effect is elicited.

The following Examples illustrate the synthesis of representative cyclosporine compounds used in the present invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

Example A. 1-[(2S)—N-Methyl-2-[tetrahydro-5-ethyl-3-methyl-2-furanyl]glycine]-cyclosporin A

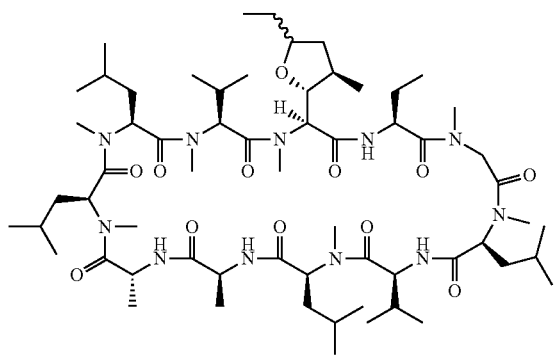 [SMILES: CCC(O)C[C@@H](C)[C@@H](C)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

a) 1-[(2S)—N-Methyl-2-[tetrahydro-5-[1-(phenylseleno)ethyl-3-methyl-2-furanyl]glycine]-cyclosporin To a solution of cyclosporine A (2.00 g, 1.66 mmol) in $CH_2Cl_2$ (50 mL) was added benzeneselenyl chloride (0.319 g, 1.66 mmol) and the resulting solution was allowed to stir at room temperature for 16h. The reaction was then concentrated under reduced pressure and purified by chromatography on a 40 g Isco RediSep cartridge using a gradient from 100% $CH_2Cl_2$ to 9:1 $CH_2Cl_2$:$CH_3OH$ to yield 1-[(2S)—N-methyl-2-[tetrahydro-5-[1-(phenylseleno)ethyl-3-methyl-2-furanyl]glycine]-cyclosporin as a mixture of diastereomers: 1.84 g (81%). 1H NMR (400 MHz, $CDCl_3$)

δ ppm 2.68 (s, 1.5 H), 2.69 (bs, 3H), 2.70 (s, 1.5 H), 3.08 (s, 1.5 H), 3.09 (s, 1.5 H), 3.17 (s, 1.5 H), 3.18 (s, 1.5 H), 3.25 (bs, 3H), 3.36 (s, 1.5 H), 3.38 (s, 1.5 H), 3.42 (s, 1.5 H), 3.50 (s, 1.5 H), 7.22-7.33 (m, 3H), 7.34-7.45 (m, 1.5 H), 7.52-7.60 (m, 2H), 7.65 (d, J=9.03 Hz, 0.5 H), 8.00 (d, J=7.27 Hz, 0.5 H), 8.04 (d, J=6.88 Hz, 0.5 H), 8.27 (d, J=9.86 Hz, 0.5 H), 8.37 (d, J=9.52 Hz, 0.5 H). MS (ESI) 680.0 [(M+2H)/2]$^+$.

b) A solution of 1-[(2S)—N-methyl-2-[tetrahydro-5-[1-(phenylseleno)ethyl-3-methyl-2-furanyl]glycine]-cyclosporin (0.088 g, 0.065 mmol) in benzene (10 mL) was charged with α,α-azoisobutyronitrile (0.021 g, 0.13 mmol) and tributyltin hydride (0.064 g, 0.22 mmol) and heated to 85C for 16 h. The reaction was then concentrated under reduced pressure and chromatographed on a 12 g Isco RediSep cartridge using a gradient from 100% CH$_2$Cl$_2$ to 9:1 CH$_2$Cl$_2$:CH$_3$OH.Subsequent lyophilization from ~8 mL 1:1 CH$_3$CN:H$_2$O yielded 1-[(2S)—N-methyl-2-[tetrahydro-5-ethyl-3-methyl-2-furanyl]glycine]-cyclosporin A as a mixture of diastereomers: 0.070 g (89%). $^1$H NMR (400 MHz, CDCl$_3$) δ ppm $^1$H NMR 2.66 (bs, 3H), 2.71 (bs, 3H), 3.08 (s, 1.5 H), 3.09 (s, 1.5 H), 3.18 (s, 1.5 H), 3.19 (s, 1.5 H), 3.25 (s, 1.5 H), 3.26 (s, 1.5 H) 3.38 (s, 1.5 H), 3.39 (s, 1.5 H), 3.49 (s, 1.5 H), 3.51 (s, 1.5 H), 7.40 (d, J=8.10 Hz, 0.5 H), 7.44 (d, J=8.10 Hz, 0.5 H), 7.48 (d, J=9.08 Hz, 0.5 H), 7.62 (d, J=8.98 Hz, 0.5 H), 8.02 (d, J=7.03 Hz, 0.5 H), 8.05 (d, J=6.88 Hz, 0.5 H), 8.31 (d, J=9.91 Hz, 0.5 H), 8.36 (d, J=9.66 Hz, 0.5 H). MS (ESI) 602.0 [(M+2H)/2]$^+$.

Example B. 1-[(2S)—N-methyl-2-[tetrahydro-5-ethenyl-3-methyl-2-furanyl]glycine]-cyclosporin A

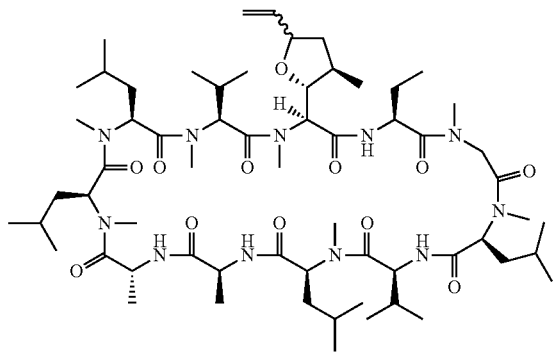 [SMILES: C=CC(O)C[C@@H](C)[C@@H](C)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

A solution of 1-[(2S)—N-methyl-2-[tetrahydro-5-[1-(phenylseleno)ethyl-3-methyl-2-furanyl]glycine]-cyclosporin (0.167 g, 0.123 mmol) in 4:1 MeOH:H$_2$O was treated with NaHCO$_3$ (0.015 g, 0.19 mmol) and sodium periodate (0.053 g, 0.25 mmol) and the mixture was stirred at room temperature for 69 h. The reaction mixture was then diluted with CH$_2$Cl$_2$, washed with aqueous saturated NaHCO$_3$ solution, dried over Na$_2$SO$_4$, filtered, and concentrated under reduced pressure. The crude product was then chromatographed on a 40 g Isco RediSep cartridge using a gradient from 100% CH$_2$Cl$_2$ to 9:1 CH$_2$Cl$_2$:CH$_3$OH. Subsequent lyophilization from ~8 mL 1:1 CH$_3$CN:H$_2$O yielded 1-[(2S)—N-methyl-2-[tetrahydro-5-ethenyl-3-methyl-2-furanyl]glycine]-cyclosporin A as a mixture of diastereomers: 0.121 g (82%). $^1$H NMR (400 MHz, CDCl$_3$) δ ppm 2.69 (s, 1.5 H), 2.70 (s, 1.5 H), 2.71 (bs, 3H), 3.08 (s, 1.5 H), 3.09 (s, 1.5 H), 3.18 (s, 1.5 H), 3.19 (s, 1.5 H), 3.25 (bs, 3H), 3.38 (s, 1.5 H), 3.39 (s, 1.5 H), 3.50 (s, 1.5 H), 3.51 (s, 1.5 H), 7.40 (d, J=8.00 Hz, 0.5 H), 7.44-7.51 (m, 1H), 7.62 (d, J=9.18 Hz, 0.5 H), 7.99 (d, J=7.08 Hz, 0.5 H), 8.06 (d, J=6.83 Hz, 0.5 H), 8.31 (d, J=9.76 Hz, 0.5 H), 8.38 (d, J=9.66 Hz, 0.5 H). MS (ESI) 601.0 [(M+2H)/2]$^+$.

Example C. 1-[(2S)—N-Methyl-2-[tetrahydro-5-ethyl-3-methyl-2-furanyl]glycine]-4-(4-hydroxy-N-methyl-L-leucine)-cyclosporin A

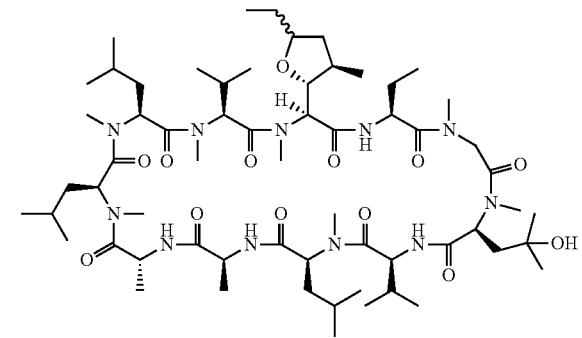 [SMILES: CCC(O)C[C@@H](C)[C@@H](C)[C@H]1C(=O)N[C@@H](CC)C(=O)N(C)CC(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

a) 1-[(2S)—N-Methyl-2-[tetrahydro-5-[1-(phenylseleno)ethyl-3-methyl-2-furanyl]glycine]-4-(4-hydroxy-N-methyl-L-leucine)-cyclosporin In a similar manner as described in Example A, using 4-(4-hydroxy-N-methyl-L-leucine)-cyclosporine A (0.500 g, 0.410 mmol) and benzeneselenyl chloride (0.079 g, 0.410 mmol) yielded 1-[(2S)—N-methyl-2-[tetrahydro-5-[1-(phenylseleno)ethyl-3-methyl-2-furanyl]glycine]-4-(4-hydroxy-N-methyl-L-leucine)-cyclosporin A as a mixture of diastereomers, 0.514 g (91%). 1H NMR (400 MHz, CDCl3) δ ppm 1H 2.68 (s, 1.5 H), 2.69 (bs, 3H), 2.71 (s, 1.5 H), 3.12 (s, 1.5 H), 3.13 (s, 1.5 H), 3.17 (s, 1.5 H), 3.18 (s, 1.5 H), 3.22 (s, 1.5 H), 3.24 (s, 1.5 H), 3.37 (s, 1.5 H), 3.39 (s, 1.5 H), 3.42 (s, 1.5 H), 3.49 (s, 1.5 H), 7.17-7.31 (m, 3H), 7.35 (d, J=8.10 Hz, 0.5 H), 7.43 (d, J=8.05 Hz, 0.5 H), 7.50-7.59 (m, 2H), 7.62 (d, J=8.88 Hz, 0.5 H), 7.84 (d, J=9.18 Hz, 0.5 H), 7.99 (d, J=7.17 Hz, 0.5 H), 8.04 (d, J=6.93 Hz, 0.5 H), 8.28 (d, J=9.76 Hz, 0.5 H), 8.34 (d, J=9.57 Hz, 0.5 H). MS (ESI) 688.0 [(M+2H)/2]+.

b) Following a similar procedure as described in Example A(b), from 1-[(2S)—N-methyl-2-[tetrahydro-5-[1-(phenylseleno)ethyl-3-methyl-2-furanyl]glycine]-4-(4-hydroxy-N-methyl-L-leucine)-cyclosporin (0.514 g, 0.374 mmol), α,α-azoisobutyronitrile (0.092 g, 0.56 mmol) and tributyltin hydride (0.163 g, 0.561 mmol) was obtained 1-[(2S)—N-methyl-2-[tetrahydro-5-ethyl-3-methyl-2-furanyl]glycine]-4-(4-hydroxy-N-methyl-L-leucine)-cyclosporin A as a mixture of diastereomers: 0.393 g (86%). $^1$H NMR (400 MHz, CDCl$_3$) δ ppm 2.69 (bs, 3H), 2.71 (bs, 3H), 3.12 (s, 1.5 H), 3.13 (s, 1.5 H), 3.18 (s, 1.5 H), 3.19 (s, 1.5 H), 3.24 (s, 1.5 H), 3.25 (s, 1.5 H), 3.39 (s, 1.5 H), 3.40 (s, 1.5 H), 3.48 (s, 1.5 H), 3.51 (s, 1.5 H), 7.39 (d, J=7.96 Hz, 0.5 H), 7.43 (d, J=7.95 Hz, 0.5 H), 7.68 (d, J=8.98 Hz, 0.5 H), 7.81 (d, J=8.98 Hz, 0.5 H), 8.02 (d, J=7.13 Hz, 0.5 H), 8.06 (d, J=6.93 Hz, 0.5 H), 8.32 (d, J=9.86 Hz, 0.5 H), 8.35 (d, J=9.61 Hz, 0.5 H). MS (ESI) 610.0 [(M+2H)/2]$^+$.

Example D. 1-[(2S)—N-methyl-2-[tetrahydro-5-ethenyl-3-methyl-2-furanyl]glycine]-4-(4-hydroxy-N-methyl-L-leucine)-cyclosporin A

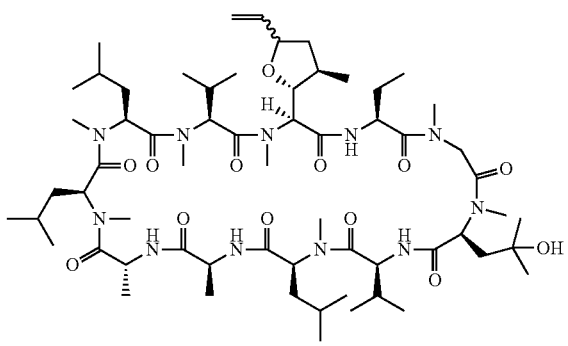

In a similar manner as described in Example B, using 1-[(2S)—N-methyl-2-[tetrahydro-5-[1-(phenylseleno)ethyl-3-methyl-2-furanyl]glycine]-4-(4-hydroxy-N-methyl-L-leucine)-cyclosporin A from Example D(a) (3.38 g, 2.46 mmol), ), NaHCO$_3$ (0.620 g, 7.38 mmol) and sodium periodate (1.05 g, 4.92 mmol) was obtained 1-[(2S)—N-methyl-2-[tetrahydro-5-ethenyl-3-methyl-2-furanyl]glycine]-4-(4-hydroxy-N-methyl-L-leucine)-cyclosporin A as a mixture of diastereomers, 2.26 g (76%). $^1$H NMR (400 MHz, CDCl$_3$) δ ppm 2.69 (s, 1.5 H), 2.69 (s, 1.5 H), 2.71 (bs, 3H), 3.12 (s, 1.5 H), 3.13 (s, 1.5 H), 3.18 (s, 1.5 H), 3.19 (s, 1.5 H), 3.25 (bs, 3H), 3.39 (s, 1.5 H), 3.39 (s, 1.5 H), 3.50 (s, 1.5 H), 3.50 (s, 1.5 H), 7.39 (d, J=8.25 Hz, 0.5 H), 7.45 (d, J=8.05 Hz, 0.5 H), 7.69 (d, J=9.03 Hz, 0.5 H), 7.81 (d, J=9.08 Hz, 0.5 H), 8.00 (d, J=6.83 Hz, 0.5 H), 8.07 (d, J=7.03 Hz, 0.5 H), 8.32 (d, J=9.86 Hz, 0.5 H), 8.37 (d, J=9.61 Hz, 0.5 H). MS (ESI) 609.0 [(M+2H)/2]$^+$.

Example E. 1-[(2S)—N-methyl-2-[tetrahydro-5-(2-hydroxyethyl)-3-methyl-2-furanyl]glycine]-4-(4-hydroxy-N-methyl-L-leucine)-cyclosporin A

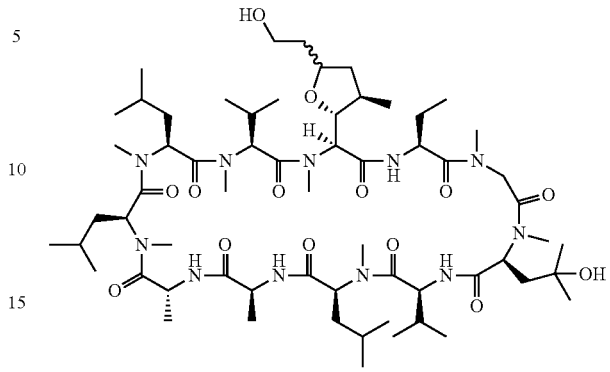

To a solution of 1-[(2S)—N-methyl-2-[tetrahydro-5-ethenyl-3-methyl-2-furanyl]glycine]-4-(4-hydroxy-N-methyl-L-leucine)-cyclosporin A (2.15 g, 1.77 mmol), in THF (100 mL) was added, dropwise, 1.0 M borane-THF solution (5.30 mL, 5.30 mmol) and the mixture was stirred at rt for 16 h. The reaction was then charged with 2.0 N NaOH (3.10 mL, 6.20 mmol) and 30% (w/w) aqueous H$_2$O$_2$ (0.90 mL, 8.85 mmol) and stirred at room temperature until complete conversion to product was achieved. The reaction was diluted with EtOAc and washed with water, dried over Na2SO4, filtered, and concentrated under reduced pressure. The crude product was purified by chromatography on a silica gel cartridge eluting with a gradient from 100% CH$_2$Cl$_2$ to 9:1 CH$_2$Cl$_2$:CH$_3$OH to yield 1-[(2S)—N-methyl-2-[tetrahydro-5-(2-hydroxyethyl)-3-methyl-2-furanyl]glycine]-4-(4-hydroxy-N-methyl-L-leucine)-cyclosporin A as a mixture of diastereomers, 1.54 g (71%). $^1$H NMR (400 MHz, CDCl$_3$) δ ppm 2.69 (s, 1.5 H) 2.71 (bs, 3H), 2.72 (s, 1.5 H), 3.08 (s, 1.5 H), 3.13 (s, 1.5 H), 3.19 (bs, 3H), 3.20 (s, 1.5 H), 3.25 (s, 1.5 H), 3.36 (s, 1.5 H), 3.39 (bs, 3H), 3.47 (s, 1.5 H), 7.19 (d, J=8.00 Hz, 0.5 H), 7.23 (d, J=8.00 Hz, 0.5 H), 7.59 (d, J=8.49 Hz, 0.5 H), 7.64 (d, J=9.08 Hz, 0.5 H), 7.73 (d, J=7.32 Hz, 0.5 H), 7.88 (d, J=7.56 Hz, 0.5 H), 7.98 (d, J=9.76 Hz, 0.5 H), 8.18 (d, J=10.05 Hz, 0.5 H). MS (ESI) 618.0 [(M+2H)/2]$^+$.

Example F. 1-[(2S)—N-methyl-2-[tetrahydro-5-ethyl-3-methyl-2-furanyl]glycine]-3-[2R-[[2-(dimethylamino)ethyl]thio]-N-methylglycine]-4-(4-hydroxy-N-methyl-L-leucine)-cyclosporin A

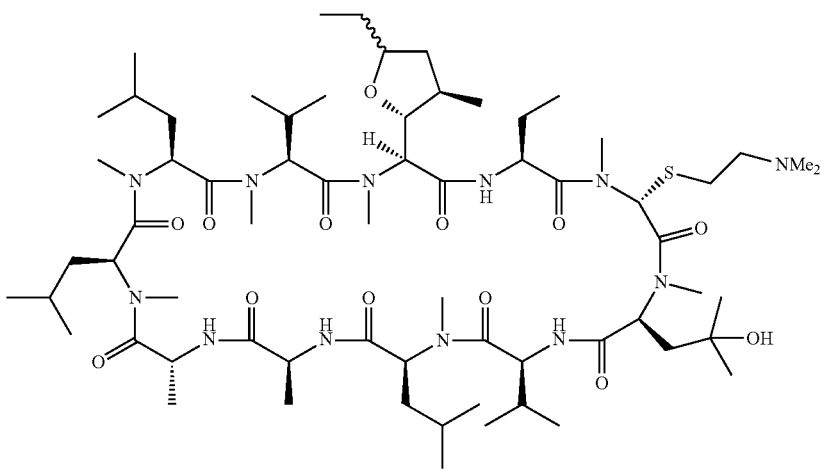 [SMILES: CCC(O)C[C@@H](C)[C@@H](C)[C@H]1C(=O)N[C@@H](CC)C(=O)N(C)[C@H](SCCN(C)C)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

1-[N-Methyl-L-2-[tetrahydro-3R-methyl-5-[1-(phenylseleno)ethyl]-2R-furanyl]glycine]-3-[2R-[[2-(dimethylamino)ethyl]thio]-N-methylglycine]-4-(4-hydroxy-N-methyl-L-leucine)-cyclosporin A Using a procedure similar to that described in Example A(a), using 3-[2R-[[2-(dimethylamino)ethyl]thio]-N-methylglycine]-4-(4-hydroxy-N-methyl-L-leucine)-cyclosporin A (0.300 g, 0.227 mmol) and benzeneselenyl chloride (0.044 g, 0.227 mmol) yielded 1-[N-methyl-L-2-[tetrahydro-3R-methyl-5-[1-(phenylseleno)ethyl]-2R-furanyl]glycine]-3-[2R-[[2-(dimethylamino)ethyl]thio]-N-methylglycine]-4-(4-hydroxy-N-methyl-L-leucine)-cyclosporin A as a mixture of diastereomers 0.287 g (86%). 1H NMR (400 MHz, CDCl$_3$) δ ppm 2.68 (s, 1.5 H), 2.68 (bs, 3H), 2.70 (s, 1.5 H), 3.16 (s, 1.5 H), 3.17 (s, 1.5 H), 3.18 (bs, 3H), 3.24 (s, 1.5 H), 3.25 (s, 1.5 H), 3.40 (s, 1.5 H), 3.41 (s, 1.5 H), 3.42 (s, 1.5 H), 3.50 (s, 1.5 H), 5.76 (s, 0.5 H), 5.93 (s, 0.5 H), 7.23-7.31 (m, 3H), 7.34 (d, J=8.05 Hz, 0.5 H), 7.39 (d, J=4.25 Hz, 0.5 H), 7.42 (d, J=4.93 Hz, 0.5 H), 7.49-7.60 (m, 2H), 7.73 (d, J=8.83 Hz, 0.5 H), 8.00 (d, J=7.22 Hz, 0.5 H), 8.03 (d, J=6.93 Hz, 0.5 H), 8.28 (d, J=9.61 Hz, 0.5 H), 8.33 (d, J=9.52 Hz, 0.5 H). MS (ESI) 739.5 [(M+2H)/2]$^+$.

Following a similar procedure as described in Example A(b), from 1-[N-methyl-L-2-[tetrahydro-3R-methyl-5-[1-(phenylseleno)ethyl]-2R-furanyl]glycine]-3-[2R-[[2-(dimethylamino)ethyl]thio]-N-methylglycine]-4-(4-hydroxy-N-methyl-L-leucine)-cyclosporin A (0.243 g, 0.164 mmol), α,α-azoisobutyronitrile (0.040 g, 0.25 mmol) and tributyltin hydride (0.072 g, 0.25 mmol) was obtained 1-[(2S)—N-methyl-2-[tetrahydro-5-ethyl-3-methyl-2-furanyl]glycine]-3-[2R-[[2-(dimethylamino)ethyl]thio]-N-methylglycine]-4-(4-hydroxy-N-methyl-L-leucine)-cyclosporin A as a mixture of diastereomers, 0.136 g (63%). 1H NMR (400 MHz, CDCl$_3$) δ ppm 2.23 (s, 6H), 2.70 (bs, 3H), 2.71 (bs, 3H), 3.16 (s, 1.5 H), 3.16 (s, 1.5 H), 3.18 (s, 1.5 H), 3.19 (s, 1.5 H), 3.24 (s, 1.5 H), 3.25 (s, 1.5 H), 3.43 (s, 1.5 H), 3.45 (s, 1.5 H), 3.49 (s, 1.5 H), 3.51 (s, 1.5 H), 5.97 (s, 0.5 H), 6.02 (s, 0.5 H), 7.37 (d, J=7.96 Hz, 0.5 H), 7.42 (d, J=7.95 Hz, 0.5 H), 7.46 (d, J=8.88 Hz, 0.5 H), 7.60 (d, J=9.42 Hz, 0.5 H), 8.05 (d, J=7.17 Hz, 0.5 H), 8.08 (d, J=6.73 Hz, 0.5 H), 8.25 (d, J=9.81 Hz, 0.5 H), 8.29 (d, J=9.66 Hz, 0.5 H). MS (ESI) 661.5 [(M+2H)/2]$^+$.

Example G. 1-[(2S)—N-methyl-2-[tetrahydro-5-ethenyl-3-methyl-2-furanyl]glycine]-3-[2R-[[2-(dimethylamino)ethyl]thio]-N-methylglycine]-4-(4-hydroxy-N-methyl-L-leucine)-cyclosporin A

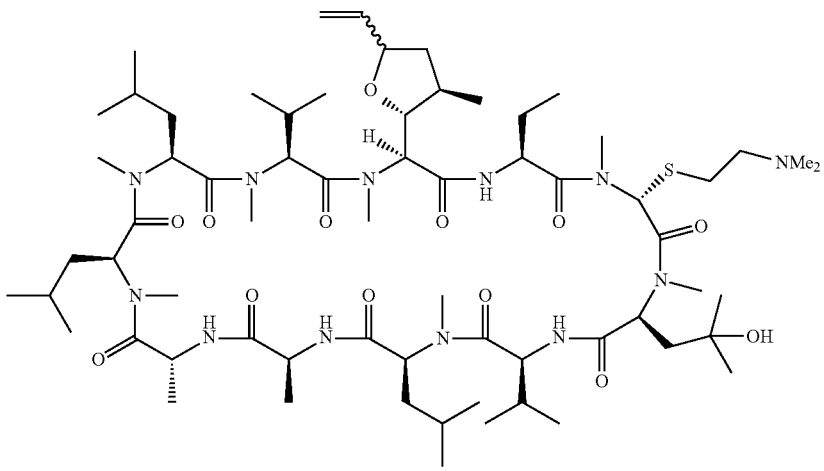 [SMILES: C=CC(O)C[C@@H](C)[C@@H](C)[C@H]1C(=O)N[C@@H](CC)C(=O)N(C)[C@H](SCCN(C)C)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

In a similar manner as described in Example B, using 1-[N-methyl-L-2-[tetrahydro-3R-methyl-5-[1-(phenylseleno)ethyl]-2R-furanyl]glycine]-3-[2R-[[2-(dimethylamino)ethyl]thio]-N-methylglycine]-4-(4-hydroxy-N-methyl-L-leucine)-cyclosporin A from Example G(a) (0.287 g, 0.194 mmol), ), NaHCO$_3$ (0.024 g, 0.29 mmol) and sodium periodate (0.046 g, 0.21 mmol) was obtained 1-[(2S)—N-methyl-2-[tetrahydro-5-ethenyl-3-methyl-2-furanyl]glycine]-3-[2R-[[2-(dimethylamino)ethyl]thio]-N-methylglycine]-4-(4-hydroxy-N-methyl-L-leucine)-cyclosporin A as a mixture of diastereomers, 0.217 g (85%). $^1$H NMR (400 MHz, CDCl$_3$) δ ppm 2.23 (s, 6H), 2.69 (s, 1.5 H), 2.70 (s, 1.5 H), 2.70 (bs, 3H), 3.16 (bs, 3H), 3.18 (s, 1.5 H), 3.19 (s, 1.5 H), 3.25 (bs, 3H), 3.43 (s, 1.5 H), 3.45 (s, 1.5 H), 3.50 (s, 1.5 H), 3.51 (s, 1.5 H), 5.97 (s, 0.5 H), 6.01 (s, 0.5 H), 7.38 (d, J=8.10 Hz, 0.5 H), 7.44 (d, J=7.96 Hz, 0.5 H), 7.48 (d, J=8.98 Hz, 0.5 H), 7.61 (d, J=8.93 Hz, 0.5 H), 8.03 (d, J=6.98 Hz, 0.5 H), 8.09 (d, J=7.13 Hz, 0.5 H), 8.26 (d, J=9.81 Hz, 0.5 H), 8.32 (d, J=9.37 Hz, 0.5 H). MS (ESI) 660.5 [(M+2H)/2]$^+$.

Example H. 1-[(2S)—N-methyl-2-[tetrahydro-5-(2-hydroxyethyl)-3-methyl-2-furanyl]glycine]-3-[2R-[[2-(dimethylamino)ethyl]thio]-N-methylglycine]-4-(4-hydroxy-N-methyl-L-leucine)-cyclosporin A chromatographed on a 40 g Isco RediSep cartridge using a gradient from 100% CH$_2$Cl$_2$ to 9:1 CH$_2$Cl$_2$:CH$_3$OH. Yield of 5c as a mixture of diastereomers: 330 mg (31%). 1H NMR (400 MHz, CDCl$_3$) δ ppm 2.23 (s, 6H), 2.69 (s, 1.5 H), 2.70 (bs, 3H), 2.71 (s, 1.5 H), 3.16 (s, 1.5 H), 3.18 (bs, 3H), 3.20 (s, 1.5 H), 3.21 (s, 1.5 H), 3.26 (s, 1.5 H), 3.42 (s, 1.5 H), 3.44 (s, 1.5 H), 3.45 (s, 1.5 H), 3.49 (s, 1.5 H), 5.99 (s, 0.5 H), 6.10 (s, 0.5 H), 7.21 (d, J=8.39 Hz, 0.5 H), 7.24-7.31 (m, 0.5 H), 7.38 (d, J=8.30 Hz, 0.5 H), 7.51 (d, J=8.88 Hz, 0.5 H), 7.81 (d, J=7.03 Hz, 0.5 H), 7.93 (d, J=7.56 Hz, 0.5 H), 8.07 (d, J=9.42 Hz, 0.5 H), 8.16 (d, J=10.05 Hz, 0.5 H). MS (ESI) 669.5 [(M+2H)/2]

4-[4-Hydroxy-N-methylleucine]cyclosporine A was prepared according to the method described in European Patent No. 484,281, the disclosure of which is specifically incorporated by reference.

HBV Entry Activity

The compounds of the present invention were tested for activity against HBV infection (entry) using methods described by Watashi et al, Hepatology, 2014 volume 59, p. 1726-1737.

Compounds of the invention were tested for activity as HBV entry inhibitors using primary human hepatocytes and a hepatoctye cell line engineered to express the NTCP transporter (HepG2-hNTCP-C$_4$). The isolation of, and the

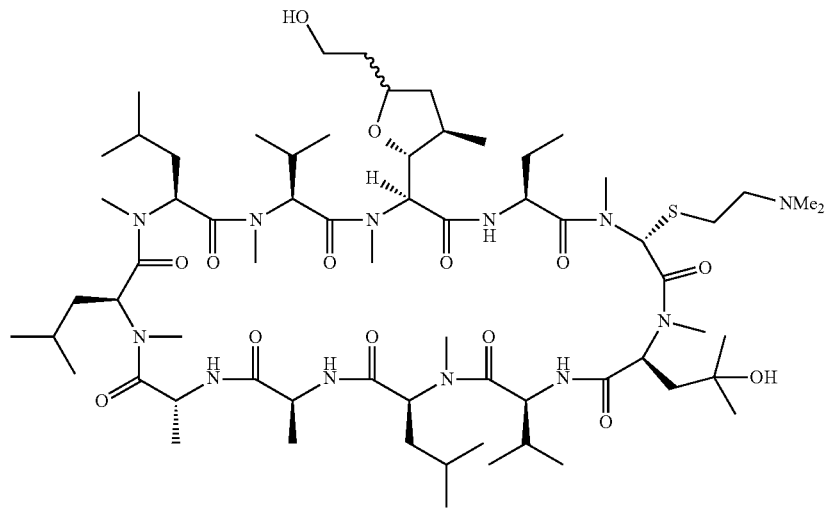 [SMILES: CC[C@@H]1NC(=O)[C@H]([C@H](C)[C@H](C)CC(O)CCO)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)(C)O)N(C)C(=O)[C@@H](SCCN(C)C)N(C)C1=O]

A solution of N,N-diisopropylethylamine (1.37 mL, 9.72 mmol, 12.0 equiv) in THF (40 mL) was chilled to −25° C., and charged with the dropwise addition of n-buytllithium (2.5 M in hexanes, 3.89 mL, 9.72 mmol, 12.0 equiv). After stirring at −25° C. for 30 min, the reaction was charged with the dropwise addition of a solution of 1-[(2S)—N-methyl-2-[tetrahydro-5-(2-hydroxyethyl)-3-methyl-2-furanyl]glycine]-4-(4-hydroxy-N-methyl-L-leucine)-cyclosporin A (Example F,1.00 g, 0.810 mmol, 1.00 equiv) in THF (5.0 mL). After stirring at −25° C. for 90 min, the reaction was charged with a solution of N,N-dimethyl-2-(p-tolylsulfonyl-sulfanyl)ethanamine (1.26 g, 4.83 mmol) in THF (5.0 mL). After stirring at −25° C. for 2 h, the reaction was allowed to warm to rt and then stir at rt for 16 h. The reaction was then charged with saturated aqueous NH$_4$Cl solution (50 mL) and extracted into EtOAc (3×200 mL). The organic fractions were then pooled, dried over Na$_2$SO$_4$, filtered, and concentrated under reduced pressure. The crude product was then culture medium, for, primary human hepatocytes (PHH) (Phoenixbio) are described by Yamasaki et al., *Drug Metab Pharmacokinet.* 2010; 25:539-550. The HepG2-hNTCP-C$_4$ cells were prepared by transfecting an expression plasmid for human NTCP (see Sugiyama et al., *Drug Metab. Dispos.* 2006, 34, pp 1575-1581). into HepG2 cells using the TransIT-LT1 (Mirus) system according to the manufacturer's instructions.

Virus used in the experiments was derived from HepAD38 cells (see Ladner et al., *Antimicrob Agents Chemother* 1997; 41, pp 1715-1720). To induce virus production, HepAD38 cells were cultured in the absence of tetracycline. Culture medium, collected every three days over the period 7-31 days post-induction, was passed through a 0.45 mm filter. Virus was precipitated using 10% PEG8000 and 2.3% NaCl. The precipitates were washed and resuspended with medium at approximately 200-fold concentration. HepG2-hNTCP-C4 cells and primary human hepatoctyes were infected with HBV at 2000-20000 (normally 6000) genome equivalents (GEq)/cell in the presence of 4% PEG8000 at 37° C. for 16 h as described by Watshi et al., *J Biol Chem* 2013; 288:31715-31727.

A representative procedure for testing compounds of the invention for activity as HBV entry inhibitors involves i) treating the appropriate cells with compound for a period of about 2 hours; ii) adding HBV or HDV virus and allowing the infection process to occur for about 16 hours; iii) washing the cells to remove free virus and the test compound; iv) culturing the cells in the absence of compound for an additional 12 days; and determining the amount of HBV in the cells by measuring HBV DNA, HBs protein in the supernatant or HBV cccDNA. This procedure can be represented by the schematic shown in FIG. 1.

Measurement of hepatitis B surface antigen protein (HBs) was carried out by ELISA using microwell antigen capture plates (Maxisorpnunc-immuno plate, Nunc #439454) were prepared by overnight incubation at 4° C. with a sheep anti-HBs antibody at 1:5000 dilution, followed by coating with 0.2% BSA/0.02% NaN3/1×PBS a t 4° C. until use. For HBs detection, samples were incubated in individual wells of the capture plates for 2 h. After washing, horseradish peroxidase-labeled rabbit anti-HBs antibody was added for an additional 2 h incubation. The substrate solution (from the HCV core ELISA kit: Ortho) was reacted for 15-60 min before the OD450 values were measured.

Figure 2:
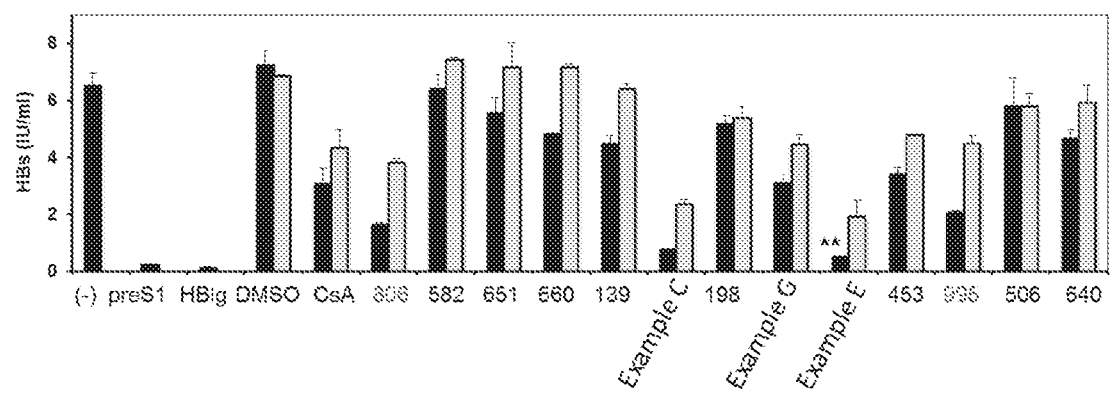
FIG. 2 shows the results for compounds of the invention tested for inhibition of HBV entry using HepG2-hNTCP-C4 cells. The effectiveness was determined by measurement of the amount of HBs protein secreted into the supernatant, showing the compounds induced a significant suppression of HBs protein production.

HBV DNA was measured by extraction from cells using a QIAamp mini kit (QIAGEN) according to the manufacturer's protocol. HBV DNA was quantified by real time PCR analysis using the primer set 5'-ACTCACCAACCTCCT-GTCCT-3' (SEQ ID NO. 1) and 5'-GA-CAAACGGGCAACATACCT-3' (SEQ ID NO. 2) and probe 5'FAM-TATCGCTGGATGTGTCTGCGGCGT-TAMRA3' (SEQ ID NO. 3). Detection of cccDNA was achieved using 5'-CGTCTGTGCCTTCTCATCTGC-3' (SEQ ID NO. 4) and 5'-GCACAGCTTGGAGGCTTGAA-3' (SEQ ID NO. 5) as primers and 5'-CTGTAGGCATAAATTGGT (MGB)-3' (SEQ ID NO. 6) as a probe. mRNAs for NTCP, CyPA, CyPB, and GAPDH were detected using a one-step RNA PCR kit (Takara) following the manufacturer's protocol. Primers are 5'-CCGGCTGAAGAACATTGAGGCACTGG-3' (SEQ ID NO. 7) and 5'-AGGGAGGAGGTGGCAAT-CAAGAGTGG-3' (SEQ ID NO. 8) for NTCP, 5'-CTC-CTTTGAGCTGTTTGCAGACAAGGTCCC-3' (SEQ ID NO. 9) and 5'-CATTTGCCATGGACAAGATGCCAG-GACCCG-3' (SEQ ID NO. 10) for CyPA, 5'-AGACTGT-TCCAAAAACAGTGGATAA-3' (SEQ ID NO. 11) and 5'-AGTGCTTCAGTTTGAAGTTCTCATC-3' (SEQ ID NO. 12) for CyPB, and 5'-CCATGGAGAAGGCTGGGG-3' (SEQ ID NO. 13) and 5'-CAAAGTTGTCATGGATGACC-3' (SEQ ID NO. 14) for GAPDH, In certain embodiments, compounds of the invention potently inhibit HBV infection in human liver cells to a greater extent than cyclosporine. When compounds of the invention were tested for inhibition of HBV entry using HepG2-hNTCP-C4 cells, and the effectiveness was determined by measurement of the amount of HBs protein secreted into the supernatant, the compounds induced a significant suppression of HBs protein production (FIG. 2).

Figure 3:
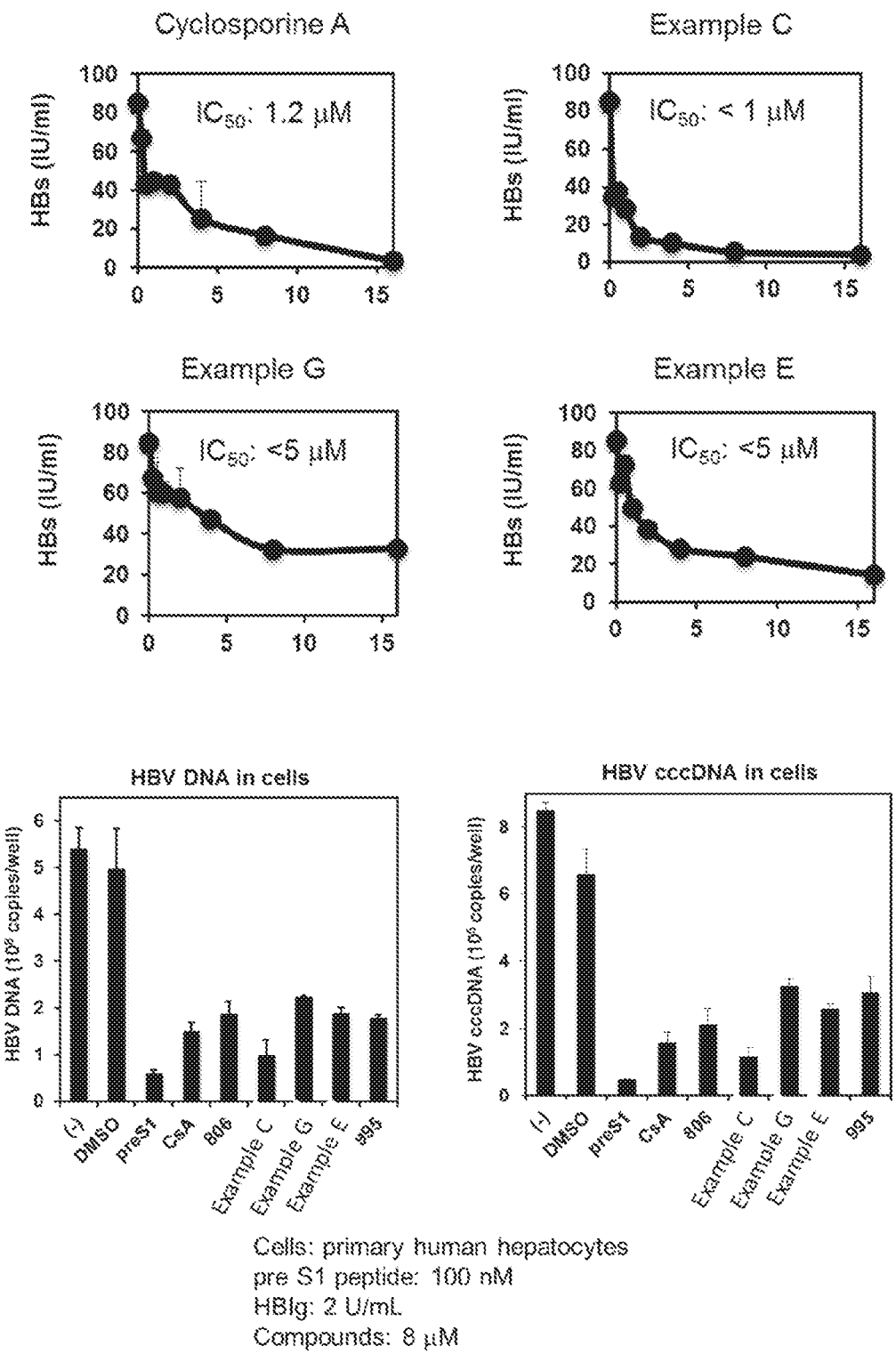
FIG. 3 shows the compounds of the invention tested for inhibition of HBV entry using primary human hepatocytes. The effectiveness was determined by measurement of the amount of HBs protein secreted into the supernatant, and by suppression of HBV DNA produced, showing the compounds induced a significant suppression of both markers.

When compounds of the invention were tested for inhibition of HBV entry using primary human hepatocytes, and the effectiveness was determined by measurement of the amount of HBs protein secreted into the supernatant, and by suppression of HBV DNA produced, the compounds induced a significant suppression of both markers (FIG. 3).

HBV Replication Activity

Figure 4:
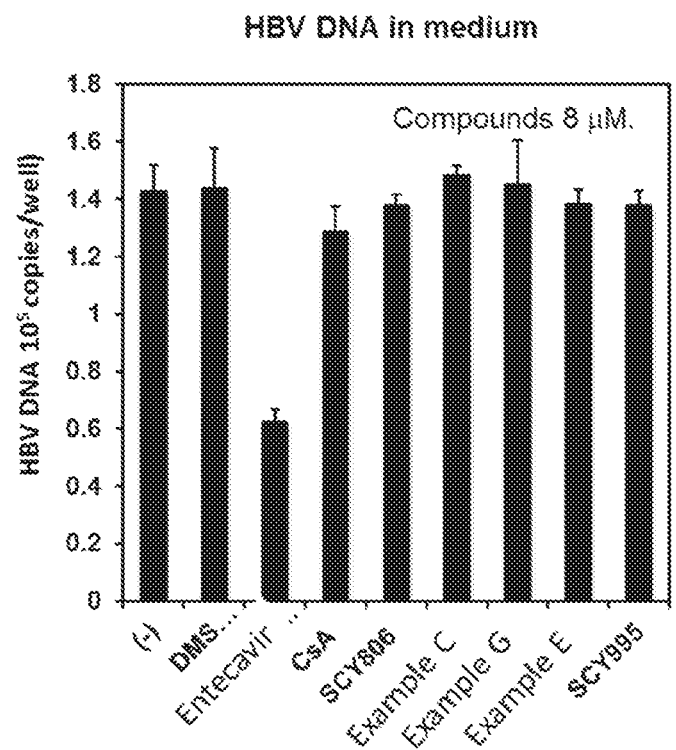
FIG. 4 shows compounds of the invention having no effect on the replication of HBV using an assay system designed to evaluate viral replication that is dependent on viral DNA.

Compounds of the invention were shown to have no effect on the replication of HBV using an assay system designed to evaluate viral replication that is dependent on viral DNA as described by Ladner et al., *Antimicrob Agents Chemother.* 1997 August; 41(8): 1715-1720 (FIG. 4)

Interaction with NTCP Membrane Transporter

Figure 5:
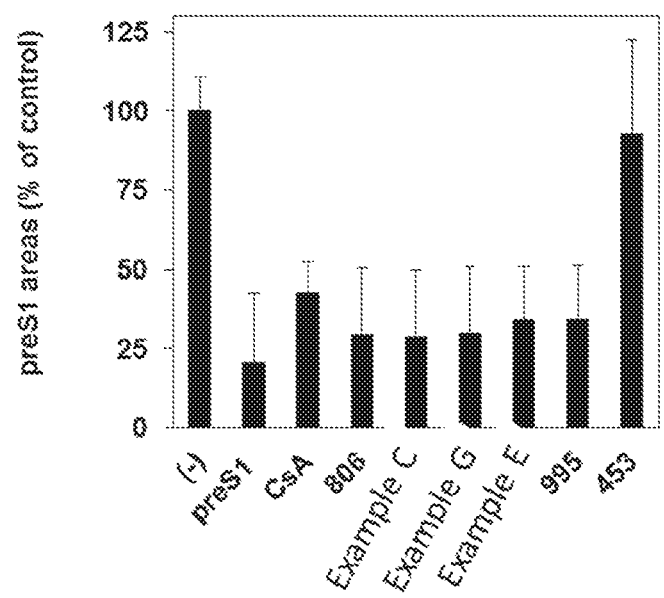
FIG. 5 shows the results for compounds of the invention tested for the ability to prevent the binding of a preS1 peptide to human NTCP.

HBV and HDV infect cells by a process that involves interaction of the HBV large surface protein with the NTCP membrane transporter expressed on cells. The preS1 peptide (see Dandri et al., *J. Hepatol*, 2013, vol. 58, pp. 861-867) represents a region of the HBV large surface protein that is involved in binding to NTCP. Compounds of the invention were tested for the ability to prevent the binding of a preS1 peptide to human NTCP. Test compounds along with a fluorescently labeled preS1 peptide sequence (preS1-TAMRA, see Watashi et al., *J Biol Chem.* 2015, vol. 290(9), pp. 5673-84) were added to HepG2-hNTCP-C4 cells for 30 minutes. The cells were washed to remove compound and unbound preS1-TAMRA and fixed with paraformaldehyde. The cells were then treated with DAPI for 1 hour, washed and subject to fluorescence detection to quantitate the amount of preS1-TAMRA. The compounds of the invention reduced the amount of preS1-TAMRA binding to hNTCP as shown in FIG. 5.

Inhibition of IL-2 Production

Compounds of the invention were tested for their activity as inhibitors of T Cell stimulation by measuring the effect on IL-2 production by Jurkat cells following PMA (phorbol 12-myristate 13-acetate) and PHA (phytohemagglutinin) co-stimulation. All new compounds were tested at 0.1 uM, 1 uM and 10 uM. Cyclosporine A (control) was also tested at 0.1 uM, 1 uM and 10 uM. All compounds to be tested were dissolved in dimethyl sulfoxide. Cytotoxicity was evaluated with parallel Alamar Blue plates. Jurkat cells were seeded at $2 \times 10^5$ cells per well in 200 μL growth media in a clear, U-bottom 96-well plate. Cells were cultured in RPMI 1640 medium, 10% fetal bovine serum, and L-Glutamine with incubation at 37° C. with 5% carbon dioxide. After 1 hour of incubation the cells were stimulated with PMA (12.5 uL of a 1 ng/mL solution in 1% DMSO/media) and PHA (12.5 uL of a 5 ug/mL solution in PBS). After 24 hours the sample supernatants were harvested and stored at −80° C. A sample of the supernatant (25 uL) was diluted with RPMI (25 uL) and the concentration of human IL-2 was determined by ELISA (Pierce, EH2IL25).

Compounds of the invention show the following effects on IL-2 production:

|  | IL-2% Inhibition | |
| --- | --- | --- |
| Compound | 1 uM | 10 uM |
| Example A | 84 | 99 |
| Example B | 43 | 99 |
| Example C | 16 | 37 |
| Example D | 8 | 23 |
| Example E | 6 | 21 |
| Example F | 2 | 5 |
| Example G | $IC_{50}$ >10 uM | |

|  | IL-2% Inhibition | |
| --- | --- | --- |
| Compound | 1 uM | 10 uM |
| Example A | 84 | 99 |
| Example B | 43 | 99 |
| Example C | 16 | 37 |
| Example D | 8 | 23 |
| Example E | 6 | 21 |

| Example F | 2 | 5 |
| Example G | IC$_{50}$ >10 uM | |

None of the compounds of the invention tested displayed cytotoxicity.

All publications and patent applications cited in this specification are herein incorporated by reference in their entireties as if each individual publication or patent application were specifically and individually indicated to be incorporated by reference. While the invention has been described in terms of various embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Primer set 1

<400> SEQUENCE: 1
actcaccaac ctcctgtcct                                              20

<210> SEQ ID NO 2
<211> LENGTH: 20
<212> TYPE: DNA
<213> ORGANISM: Artificial Sequence
<220> FEATURE:
<223> OTHER INFORMATION: Primer set 1

<400> SEQUENCE: 2
gacaaacggg caacatacct                                              20

<210> SEQ ID NO 3
<211> LENGTH: 24
<212> TYPE: DNA
<213> ORGANISM: Artificial Sequence
<220> FEATURE:
<223> OTHER INFORMATION: Probe - primer set 1
<220> FEATURE:
<221> NAME/KEY: misc_binding
<222> LOCATION: (1)..(1)
<223> OTHER INFORMATION: FAM (Fluroescein) fluorescent dye is attached
      to 5' of sequence
<220> FEATURE:
<221> NAME/KEY: misc_binding
<222> LOCATION: (24)..(24)
<223> OTHER INFORMATION: TAMRA (Carboxytetramethylrhodamine) fluoroscent
      dye which is a derivative of Rhodamine is provided at 3' of
      sequence

<400> SEQUENCE: 3
tatcgctgga tgtgtctgcg gcgt                                         24

<210> SEQ ID NO 4
<211> LENGTH: 21
<212> TYPE: DNA
<213> ORGANISM: Artificial Sequence
<220> FEATURE:
<223> OTHER INFORMATION: cccDNA primer 1

<400> SEQUENCE: 4
cgtctgtgcc ttctcatctg c                                            21

<210> SEQ ID NO 5
<211> LENGTH: 20
<212> TYPE: DNA
<213> ORGANISM: Artificial Sequence
<220> FEATURE:
```

<223> OTHER INFORMATION: cccDNA primer 2

<400> SEQUENCE: 5
gcacagcttg gaggcttgaa                                           20

<210> SEQ ID NO 6
<211> LENGTH: 18
<212> TYPE: DNA
<213> ORGANISM: Artificial Sequence
<220> FEATURE:
<223> OTHER INFORMATION: cccDNA probe
<220> FEATURE:
<221> NAME/KEY: misc_binding
<222> LOCATION: (18)..(18)
<223> OTHER INFORMATION: MGB (minor groove binder group) is provided at
      3' of sequence

<400> SEQUENCE: 6
ctgtaggcat aaattggt                                             18

<210> SEQ ID NO 7
<211> LENGTH: 26
<212> TYPE: DNA
<213> ORGANISM: Artificial Sequence
<220> FEATURE:
<223> OTHER INFORMATION: RNA PCR primer NTCP

<400> SEQUENCE: 7
ccggctgaag aacattgagg cactgg                                    26

<210> SEQ ID NO 8
<211> LENGTH: 26
<212> TYPE: DNA
<213> ORGANISM: Artificial Sequence
<220> FEATURE:
<223> OTHER INFORMATION: RNA PCR primer NTCP

<400> SEQUENCE: 8
agggaggagg tggcaatcaa gagtgg                                    26

<210> SEQ ID NO 9
<211> LENGTH: 30
<212> TYPE: DNA
<213> ORGANISM: Artificial Sequence
<220> FEATURE:
<223> OTHER INFORMATION: RNA PCR primer CyPA

<400> SEQUENCE: 9
ctcctttgag ctgtttgcag acaaggtccc                                30

<210> SEQ ID NO 10
<211> LENGTH: 30
<212> TYPE: DNA
<213> ORGANISM: Artificial Sequence
<220> FEATURE:
<223> OTHER INFORMATION: RNA PCR primer CyPA

<400> SEQUENCE: 10
catttgccat ggacaagatg ccaggacccg                                30

<210> SEQ ID NO 11
<211> LENGTH: 25
<212> TYPE: DNA
<213> ORGANISM: Artificial Sequence
<220> FEATURE:
<223> OTHER INFORMATION: RNA PCR primer CyPB

```
<400> SEQUENCE: 11
agactgttcc aaaaacagtg gataa                                              25

<210> SEQ ID NO 12
<211> LENGTH: 25
<212> TYPE: DNA
<213> ORGANISM: Artificial Sequence
<220> FEATURE:
<223> OTHER INFORMATION: RNA PCR primer CyPB

<400> SEQUENCE: 12
agtgcttcag tttgaagttc tcatc                                              25

<210> SEQ ID NO 13
<211> LENGTH: 18
<212> TYPE: DNA
<213> ORGANISM: Artificial Sequence
<220> FEATURE:
<223> OTHER INFORMATION: RNA PCR primer GAPDH

<400> SEQUENCE: 13
ccatggagaa ggctgggg                                                      18

<210> SEQ ID NO 14
<211> LENGTH: 20
<212> TYPE: DNA
<213> ORGANISM: Artificial Sequence
<220> FEATURE:
<223> OTHER INFORMATION: RNA PCR primer GAPDH

<400> SEQUENCE: 14
caaagttgtc atggatgacc                                                    20
```

What we claim is:

1. A compound of general formula (I):

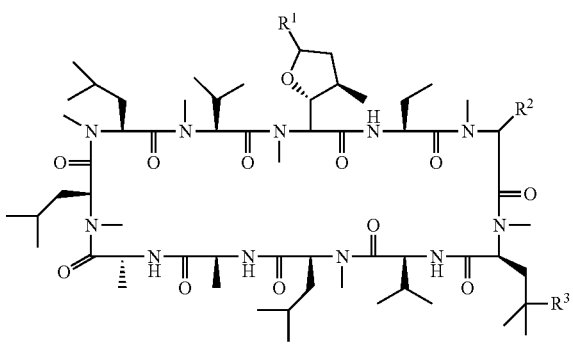

(I)

or a pharmaceutically acceptable salt or solvate thereof, wherein:

$R^1$ represents —$CH_2CH_3$, —$CHCH_2$ or —$CH_2CH_2OH$;

$R^2$ represents hydrogen; $C_1$-$C_6$-alkyl; or $XR^5$;

$R^3$ represents hydrogen or hydroxyl, with the proviso that when $R^2$ and $R^3$ are both hydrogen then $R^1$ cannot be —$CH_2CH_2OH$;

X represents sulfur or oxygen;

$R^5$ represents straight- or branched-chain alkyl having from one to six carbon atoms, optionally substituted by one or more groups selected from the group consisting of halogen; hydroxy; alkoxy; and —$NR^6R^7$;

$R^6$ and $R^7$, which may be the same or different, each represent:

hydrogen; methyl or ethyl.

2. The compound according to claim 1 in which $R^3$ represents hydroxyl.

3. The compound according to claim 1 in which $R^2$ represents hydrogen or $XR^5$.

4. The compound according to claim 1 in which $R^2$ represents —$SCH_2CH_2NMe_2$.

5. The compound according to claim 1 which is selected from

1-[(2S)—N-Methyl-2-[tetrahydro-5-ethyl-3-methyl-2-furanyl]glycine]-cyclosporin A, 1-[(2S)—N-methyl-2-[tetrahydro-5-ethenyl-3-methyl-2-furanyl]glycine]-cyclosporin A, 1-[(2S)—N-methyl-2-[tetrahydro-5-ethyl-3-methyl-2-furanyl]glycine]-4-(4-hydroxy-N-methyl-L-leucine)-cyclosporin A, 1-[(2S)—N-methyl-2-[tetrahydro-5-ethenyl-3-methyl-2-furanyl]glycine]-4-(4-hydroxy-N-methyl-L-leucine)-cyclosporin A, 1-[(2S)—N-methyl-2-[tetrahydro-5-(2-hydroxyethyl)-3-methyl-2-furanyl]glycine]-4-(4-hydroxy-N-methyl-L-leucine)-cyclosporin A, 1-[(2S)—N-methyl-2-[tetrahydro-5-ethyl-3-methyl-2-furanyl]glycine]-3-[2R-[[2-(dimethylamino)ethyl]thio]-N-methylglycine]-4-(4-hydroxy-N-methyl-L-leucine)-cyclosporin A, 1-[(2S)—N-methyl-2-[tetrahydro-5-ethenyl-3-methyl-2-furanyl]glycine]-3-[2R-[[2-(dimethylamino)ethyl]thio]-N-methylglycine]-4-(4-hydroxy-N-methyl-L-leucine)-cyclosporin A, and 1-[(2S)—N-methyl-2-[tetrahydro-5-(2-hydroxyethyl)-3-methyl-2-furanyl]glycine]-3-[2R-[[2-(dimethylamino)ethyl]thio]-N-methylglycine]-4-(4-hydroxy-N-methyl-L-leucine)-cyclosporin A.

6. A composition comprising a compound of general formula (I) as defined in claim 1, or a pharmaceutically acceptable salt or solvate thereof, and a pharmaceutically acceptable excipient, carrier or diluent.

7. The composition of claim 6 further comprising one or more additional compounds effective for the treatment or prevention of HBV or HDV.

8. A composition comprising a compound of general formula (I):

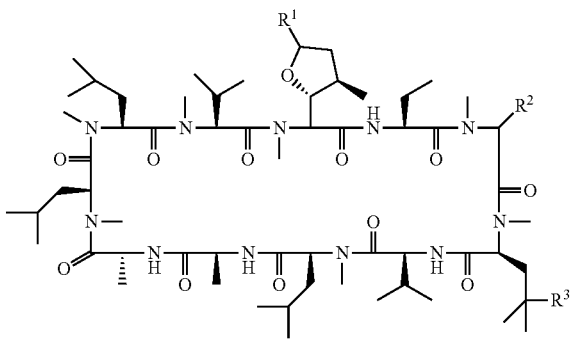

(I)

or a pharmaceutically acceptable salt or solvate thereof, wherein:

$R^1$ represents —CH$_2$CH$_3$, —CHCH$_2$ or —CH$_2$CH$_2$OH;

$R^2$ represents hydrogen; alkyl; and XR$^5$;

$R^3$ represents hydrogen or hydroxyl;

X represents sulfur or oxygen;

$R^5$ represents straight- or branched-chain alkyl, optionally substituted by one or more groups selected from the group consisting of halogen; hydroxy; alkoxy; and —NR$^6$R$^7$;

$R^6$ and $R^7$, which may be the same or different, each represent:

hydrogen; methyl; or ethyl;

and a pharmaceutically acceptable excipient, carrier or diluent.

9. The composition of claim 8 further comprising one or more additional compounds effective for the treatment or prevention of HBV or HDV.

* * * * *